United States Patent
Knight et al.

(10) Patent No.: US 10,232,018 B2
(45) Date of Patent: Mar. 19, 2019

(54) ACTH FOR TREATMENT OF ACUTE RESPIRATORY DISTRESS SYNDROME

(71) Applicant: MALLINCKRODT ARD IP LIMITED, Blanchardstown (IE)

(72) Inventors: James Knight, Oakland, CA (US); Steve Cartt, Hayward, CA (US); David Young, Ellicott City, MD (US); Patrice Becker, Baltimore, MD (US)

(73) Assignee: Mallinckrodt ARD IP Limited, Blanchardstown (IE)

( * ) Notice: Subject to any disclaimer, the term of this patent is extended or adjusted under 35 U.S.C. 154(b) by 86 days.

(21) Appl. No.: 14/214,449

(22) Filed: Mar. 14, 2014

(65) Prior Publication Data

US 2014/0322226 A1    Oct. 30, 2014

Related U.S. Application Data

(60) Provisional application No. 61/785,631, filed on Mar. 14, 2013.

(51) Int. Cl.
| | |
|---|---|
| A61K 9/00 | (2006.01) |
| A23L 33/00 | (2016.01) |
| A61K 38/22 | (2006.01) |
| A61K 38/35 | (2006.01) |
| A61K 45/06 | (2006.01) |

(52) U.S. Cl.
CPC ............ *A61K 38/22* (2013.01); *A23L 33/30* (2016.08); *A61K 9/0014* (2013.01); *A61K 9/0031* (2013.01); *A61K 9/0043* (2013.01); *A61K 9/0053* (2013.01); *A61K 9/0078* (2013.01); *A61K 38/35* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,598,122 A | 8/1971 | Zaffaroni | |
| 3,598,123 A | 8/1971 | Zaffaroni | |
| 3,710,795 A | 1/1973 | Higuchi et al. | |
| 3,731,683 A | 5/1973 | Zaffaroni | |
| 3,742,951 A | 7/1973 | Zaffaroni | |
| 3,814,097 A | 6/1974 | Ganderton et al. | |
| 3,921,636 A | 11/1975 | Zaffaroni | |
| 3,972,995 A | 8/1976 | Tsuk et al. | |
| 3,993,072 A | 11/1976 | Zaffaroni | |
| 3,993,073 A | 11/1976 | Zaffaroni | |
| 3,996,934 A | 12/1976 | Zaffaroni | |
| 4,031,894 A | 6/1977 | Urquhart et al. | |
| 4,060,084 A | 11/1977 | Chandrasekaran et al. | |
| 4,069,307 A | 1/1978 | Higuchi et al. | |
| 4,077,407 A | 3/1978 | Theeuwes et al. | |
| 4,201,211 A | 5/1980 | Chandrasekaran et al. | |
| 4,229,447 A | 10/1980 | Porter | |
| 4,230,105 A | 10/1980 | Harwood | |
| 4,292,299 A | 9/1981 | Suzuki et al. | |
| 4,292,303 A | 9/1981 | Keith et al. | |
| 4,476,116 A | 10/1984 | Anik | |
| 4,596,795 A | 6/1986 | Pitha | |
| 4,755,386 A | 7/1988 | Hsiao et al. | |
| 4,871,549 A | 10/1989 | Ueda et al. | |
| 5,011,692 A | 4/1991 | Fujioka et al. | |
| 5,017,381 A | 5/1991 | Maruyama et al. | |
| 5,116,817 A | 5/1992 | Anik | |
| 5,229,135 A | 7/1993 | Philippon et al. | |
| 5,260,068 A | 11/1993 | Chen | |
| 5,260,069 A | 11/1993 | Chen | |
| 5,336,168 A | 8/1994 | Sibalis | |
| 5,508,040 A | 4/1996 | Chen | |
| 5,567,441 A | 10/1996 | Chen | |
| 5,665,378 A | 9/1997 | Davis et al. | |
| 5,739,136 A | 4/1998 | Ellinwood, Jr. et al. | |
| 5,837,280 A | 11/1998 | Kenealy et al. | |
| 5,837,284 A | 11/1998 | Mehta et al. | |
| 5,840,329 A | 11/1998 | Bai | |
| 5,858,401 A | 1/1999 | Bhalani et al. | |
| 5,869,090 A | 2/1999 | Rosenbaum | |
| 6,391,452 B1 | 5/2002 | Antonsen et al. | |
| 6,667,048 B1 | 12/2003 | Lambert et al. | |
| 6,923,983 B2 | 8/2005 | Morgan et al. | |
| 6,929,801 B2 | 8/2005 | Klose et al. | |
| 6,946,144 B1 | 9/2005 | Jordan | |
| 6,960,563 B2 | 11/2005 | Egbaria et al. | |
| 8,039,435 B2 | 10/2011 | Dong et al. | |
| 8,133,713 B2 | 3/2012 | Otsuka et al. | |
| 8,563,000 B2 | 10/2013 | Dong et al. | |
| 2010/0204131 A1* | 8/2010 | Bevec | 514/13 |
| 2011/0183886 A1 | 7/2011 | Dong et al. | |

FOREIGN PATENT DOCUMENTS

| | | |
|---|---|---|
| WO | WO 2002/069905 A2 | 9/2002 |
| WO | WO 2008/033395 A2 | 3/2008 |
| WO | WO 2008049011 A2 * | 4/2008 |
| WO | WO 2011/143152 A2 | 11/2011 |
| WO | WO 2014/153221 A2 | 9/2014 |
| WO | WO 2014/153221 A3 | 12/2014 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Guido et al (Curr Med Chem. 2008;15(1):37-46).*
Clark et al (J. Med. Chem., 2014, 57 (12), pp. 5023-5038).*
American Lung Association (retrieved from http://www.lung.org/assets/documents/publications/lung-disease-data/ldd08- chapters/LDD-08-ARDS.pdf on May 18, 2015; published with Lung Disease Data 2008).*

(Continued)

*Primary Examiner* — Brian Gangle
*Assistant Examiner* — Andrew K McCollum

(57) ABSTRACT

Provided herein are methods of treatment of acute respiratory distress syndrome comprising administration of adrenocorticotropic hormone (ACTH). or fragment, analog, complex or aggregate thereof, or any combination thereof, to an individual in need thereof.

21 Claims, 9 Drawing Sheets

Specification includes a Sequence Listing.

(56) References Cited

OTHER PUBLICATIONS

Baumann at al., "Prolonged corticotropic action of synthetic human ACTH in man." J Clin Endocrinol Metab. Jan. 1976;42(1):160-163.
Burbelo et al., "Rapid induction of autoantibodies during ARDS and septic shock." J Transl Med. Oct. 14, 2010;8:97 (9 pages).
Ceriani et al., "The neuropeptide alpha-melanocyte-stimulating hormone inhibits experimental arthritis in rats." Neuroimmunomodulation. Jan. 1994;1(1):28-32.
Chiou & Riegelman, "Pharmaceutical Application of Solid Dispersion Systems," Journal of Pharmaceuticals Sciences, vol. 60, No. 9, pp. 1281-1302 (1971).
Fudala et al., "Anti-interleukin-8 autoantibody:interleukin-8 immune complexes in acute lung injury/acute respiratory distress syndrome." Clinical Science, 2008, 114, 403-412.
Hofmann et al. "Correlation of adrenocorticotropic activity of ACTH analogs with degree of binding to an adrenal cortical particulate preparation." Proc Natl Acad Sci U S A. Oct. 1970;67(2):829-836.
IUPHAR Database ligand ID No. 3633, URL <http://www.iuphar-db.org/DATABASE/LigandDisplayForward?tab=biology&ligandId=3633> accessed Oct. 16, 2014.
Johnson, et al., "Acute Lung Injury: Epidemiology, Pathogenesis, and Treatment." J Aerosol Med Pulm Drug Deliv. Aug. 2010; 23(4): 243-252.
Karsi et al., "Linkage Mapping of the Channel Catfish *Proopiomelanocortin* (POMC) gene," International Society for Animal Genetics, 36 (169-190), pp. 171-173 (2005).
Klimek et al., "Reduction of RDS mortality in newborns after administration of synthetic ACTH to the mothers." Ginekol Pol. May 1983;54(5):341-343.
Krieger, D., "ACTH Action," Ch. 3 in Cushing's Syndrome: Monographs on Endocrinology vol. 22, 1982, pp. 23-32.
Lipton et al., "Antiinflammatory effects of the neuropeptide alpha-MSH in acute, chronic, and systemic inflammation." Ann N Y Acad Sci. Nov. 25, 1994;741:137-148.
Maneta-Peyret et al., "Autoantibodies to lipids in bronchoalveolar lavage fluid of patients with acute respiratory distress syndrome." Crit Care Med. Oct. 2001;29(10):1950-1954.
Marik et al., "Glucocorticoid treatment in acute lung injury and acute respiratory distress syndrome." Crit Care Clin. 2011;27(3):589-607.
Matthay et al., "The acute respiratory distress syndrome: pathogenesis and treatment." Annual Rev. Pathol. Mech. Dis., 2011, 6, 147-163.
Meduri et al., "Effect of prolonged methylprednisolone therapy in unresolving acute respiratory distress syndrome: A randomized controlled trial." JAMA. 1998;280(2):159-165.
Pan et al., "2,3-Diaryl-5-anilino[1,2,4]thiadiazoles as melanocortin MC4 receptor agonists and their effects on feeding behavior in rats." Bioorg Med Chem. Jan. 17, 2003;11(2):185-192.
PCT/US2014/029695 International Search Report and Written Opinion dated Oct. 9, 2014.
Schiöth et al., "Characterisation of melanocortin receptor subtypes by radioligand binding analysis." Eur J Pharmacol. 1995;288(3):311-317.
Ware LB, Matthay MA. "The acute respiratory distress syndrome." N Engl J Med 2000;342:1334-1349.
Watterberg et al., "Chorioamnionitis, cortisol, and acute lung disease in very low birth weight infants." Pediatrics. Feb. 1997;99(2):E6.
PCT/US2014/029695 International Preliminary Report on Patentability dated Sep. 24, 2015.
Office action dated Jun. 27, 2017 from related European Application No. 14721142.9, 4 pgs.
Office action dated Mar. 22, 2018 from related European Application No. 14721142.9, 3 pgs.

\* cited by examiner

FIG. 6

|  | # normal/# observed (percent normal) | |
| --- | --- | --- |
|  | Day 3 | Day 6 |
| Saline | 12/12 (100) | 6/6 (100) |
| LPS + Placebo | 8/10 (80) | 4/5 (80) |
| LPS + Acthar 80U/kg BID | 10/12 (83) | 6/6 (100) |
| LPS + Acthar 160U/kg QD | 9/10 (90) | 6/6 (100) |

ACTH FOR TREATMENT OF ACUTE RESPIRATORY DISTRESS SYNDROME

CROSS-REFERENCE TO RELATED APPLICATIONS

This application claims the benefit of U.S. Provisional Patent Application Ser. No. 61/785,631, filed on Mar. 14, 2013, which is herein incorporated by reference in its entirety.

SEQUENCE LISTING

The instant application contains a Sequence Listing which has been submitted in ASCII format via EFS-Web. Said ASCII copy, named 32103_732_201_ST25.txt and created on Jul. 10, 2014, is 3,959 bytes in size and is hereby incorporated by reference in its entirety.

BACKGROUND OF THE INVENTION

Acute respiratory distress syndrome (ARDS) is a type of severe acute lung dysfunction affecting all or most of both lungs and can be a severe complication of any number of factors such as pneumonia, sepsis, trauma, or inhaled irritants. Direct and indirect insults to the parenchyma or vasculature of the lungs are typically followed by rapid-onset respiratory failure. ARDS is a serious condition with associated high mortality that afflicts approximately 200,000 people in the United States each year, leading to approximately 75,000 deaths. A number of clinical trials of treatments for ARDS have been conducted and to date none have been proved highly effective; therefore there is a great need for new, more effective treatments.

SUMMARY OF THE INVENTION

Described herein are methods of preventing or treating an individual diagnosed with, suspected of having, or at risk for developing acute respiratory distress syndrome (ARDS) comprising administration of an adrenocorticotropic hormone (ACTH) peptide, or fragment, analog, complex or aggregate thereof, or any combination thereof, to an individual in need thereof. In some embodiments, the methods described herein can be used to treat an individual diagnosed with ARDS comprising administration of an adrenocorticotropic hormone (ACTH) peptide, or fragment, analog, complex or aggregate thereof, or any combination thereof, to an individual in need thereof at a therapeutically effective amount and interval. In some embodiments, the treatments described herein are prophylactic and used to prevent ARDS. In some embodiments, the treatments described herein are acute and used to treat ARDS.

In some embodiments, provided herein is a method of treating an individual diagnosed with, suspected of having, or at risk for developing ARDS comprising administration of an adrenocorticotropic hormone (ACTH) peptide, or fragment, analog, complex or aggregate thereof, or any combination thereof, to an individual in need thereof.

In some embodiments, provided herein is a method of treating an individual diagnosed with or suspected of having, or preventing in an individual at risk for developing, acute respiratory distress syndrome (ARDS) comprising administration of a therapeutically effective amount of an adrenocorticotropic hormone (ACTH) peptide, or fragment, analog, complex or aggregate thereof, or any combination thereof, to an individual in need thereof, provided that the adrenocorticotropic hormone (ACTH) peptide, or fragment, analog, complex or aggregate thereof, or any combination thereof, does not comprise α-MSH.

In some embodiments, provided herein is the use of an adrenocorticotropic hormone (ACTH) peptide, or fragment, analog, complex or aggregate thereof, or any combination thereof for treating an individual diagnosed with, suspected of having, or at risk for developing ARDS.

In some embodiments, the ACTH peptide or fragment, analog, complex or aggregate thereof, or any combination thereof is administered as a first dose and one or more subsequent doses. In some embodiments, the first dose of the ACTH peptide or fragment, analog, complex or aggregate thereof, or any combination thereof, is between about 10 U and about 150 U. In some embodiments, the first dose of the ACTH peptide or fragment, analog, complex or aggregate thereof, or any combination thereof, is between about 10 U and about 100 U. In some embodiments, the first dose of the ACTH peptide or fragment, analog, complex or aggregate thereof, or any combination thereof, is between about 10 U and about 150 U, and the one or more subsequent doses of ACTH peptide or fragment, analog, complex or aggregate thereof, or any combination thereof, are between about 20% and about 80% of the first dose. In some embodiments, the first dose of the ACTH peptide or fragment, analog, complex or aggregate thereof, or any combination thereof, is between about 10 U and about 150 U, and the one or more subsequent doses of ACTH peptide or fragment, analog, complex or aggregate thereof, or any combination thereof, are between about 20% and about 60% of the first dose.

In some embodiments, the one or more subsequent doses of the ACTH peptide or fragment, analog, complex or aggregate thereof, or any combination thereof, are administered multiple times a day, about every day, about every 2 days, about every 5 days, about every week, about every two weeks, about every three weeks, about every month, about every two months, or any combination thereof.

In some embodiments, the ACTH peptide or fragment, analog, complex or aggregate thereof, or any combination thereof, is administered as an initial phase of one or more doses and a subsequent phase of one or more doses. In some cases, the initial phase is one, two, three, four, five, six, seven, eight, nine, or ten doses. In some cases, the initial phase is from one to two, one to three, one to four, one to five, one to six, one to seven, one to eight, one to nine, or one to ten doses. In some embodiments, the dosing intervals of the initial phase and the subsequent are the same. In some embodiments, the dosing intervals of the initial phase and the subsequent are different. In some embodiments, the ACTH peptide or fragment, analog, complex or aggregate thereof, or any combination thereof, is administered as an initial phase at daily intervals and a subsequent phase at intervals greater than one day. In some embodiments, the one or more of the doses of the subsequent phase are administered at intervals of every other day or once every two days, once every three days, once every four days, once every five days, once every six days, once a week, twice a week, three times a week, four times a week, five times a week, six times a week, or once every two weeks, once every three weeks, once every four weeks, once every month, one every two months, or once every three months. In some embodiments, the ACTH peptide or fragment, analog, complex or aggregate thereof, or any combination thereof, is administered as an initial phase of from one to five doses at daily intervals and a subsequent phase of one or more doses administered at intervals greater than one day. In some embodiments, each of the one to five doses of the initial phase is between about 10 U and about 150 U. In some embodiments, each of the one to five doses of the initial phase is between about 30 U and about 100 U. In some embodiments, each of the one to five doses of the initial phase is between about 10 U and about 100 U. In some embodiments, each of the one or more doses of the subsequent phase is between about 30 U and about 100 U. In some embodiments, each of the one to five doses of the initial phase is about 64 U, and each of the one or more doses of the subsequent phase is about 32 U. In some embodiments, each of the one to five doses of the initial phase is between about 30 U and about 100 U, and each of the one or more doses of the subsequent phase is between about 20% and about 100% of the one to five doses of the initial phase. In some embodiments, each of the one to five doses of the initial phase is between about 10 U and about 150 U, and each of the one or more doses of the subsequent phase is between about 10 U and about 80 U. In some embodiments, each of the one to five doses of the initial phase is between about 45 U and about 100 U, and each of the one or more doses of the subsequent phase is between about 10 U and about 80 U. In some embodiments, each of the one to five doses of the initial phase is between about 60 U and about 100 U, and each of the one or more doses of the subsequent phase is between about 20 U and about 60 U. In some embodiments, each of the one to five doses of the initial phase is about 80 U, and each of the one or more doses of the subsequent phase is about 40 U.

In some embodiments, the dosing regimen is designed to avoid steroidogenic effects of the ACTH peptide or fragment, analog, complex or aggregate thereof, and lessen the risk of, or avoid, critical illness polymyopathy (CIM) and/or critical illness polyneuropathy (CIP), which are overlapping syndromes of widespread muscle weakness (CIM) and neurological dysfunction (CIP) that can develop as complications in critically ill patients receiving intensive care.

In one embodiment, the dose for a patient (e.g., an intensive care patient) comprises a first phase of dosing of about 4 to about 10 days duration wherein a patient receives a daily dose of 64 U daily or in a divided dose of 32 U administered at a selected interval within each day, followed by one or more subsequent phases of about 4 to about 10 days duration each wherein each successive phase of doses is about 50% of the dose of the preceding phase, followed by a final phase wherein the dose of the preceding phase in maintained and administered at intervals of every other day.

In one embodiment, the dose for a patient (e.g., an intensive care patient) comprises a first phase of dosing of about 7 days duration wherein the dose is administered as 64 U once per day or 32 U twice a day, followed by a second phase of about 7 days duration wherein the daily, or twice daily, dose is reduced by about 50%, followed by a third phase of about 7 days duration wherein the daily, or twice daily, dose of the second phase is reduced by about 50% and followed by a fourth phase of about 7 days, the dose of the third phase is administered every other day. In some embodiments, the ACTH peptide or fragment, analog, complex or aggregate thereof, or any combination thereof, is an $ACTH_{1-39}$ peptide having the formula:

```
                                          (SEQ ID NO: 1)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24  25   26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof, wherein $X_{aa1}$ is Asp or Asn; and $X_{aa2}$ is Gln or Glu.

In some embodiments, the ACTH peptide or fragment, analog, complex or aggregate thereof, or any combination thereof, is an $ACTH_{1-39}$ peptide having the formula:

```
                                          (SEQ ID NO: 2)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, the ACTH peptide or fragment, analog, complex or aggregate thereof, or any combination thereof, is an $ACTH_{1-39}$ peptide having the formula:

```
                                          (SEQ ID NO: 3)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, the ACTH peptide or fragment, analog, complex or aggregate thereof, or any combination thereof, is an $ACTH_{1-39}$ peptide having the formula:

```
                                          (SEQ ID NO: 4)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23  24 25  26  27  28  29  30

Leu-Ala-Glu-Ala-Phe-Pro-Leu-Glu-Phe-OH
 31  32  33  34  35  36  37 38  39
``` or a fragment, complex, aggregate, or analog thereof, or any combination thereof.

In some embodiments, the ACTH peptide or fragment, analog, complex or aggregate thereof, or any combination thereof, is an $ACTH_{1-39}$ peptide having the formula:

```
                                              (SEQ ID NO: 5)
H-Ser-Tyr-Ser-Met-Glu-His-Phe-Arg-Trp-Gly-
    1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, the ACTH peptide or fragment, analog, complex or aggregate thereof, or any combination thereof, is an $ACTH_{1-24}$ peptide having the formula:

```
                                              (SEQ ID NO: 6)
H-Ser-Tyr-Ser-Met-Glu-His-Phe-Arg-Trp-Gly-
    1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro
 21  22  23  24
``` or a fragment, complex, aggregate, or analog thereof, or any combination thereof.

In some embodiments, the ACTH peptide or fragment, analog, complex or aggregate thereof, or any combination thereof, is an $ACTH_{1-17}$ peptide having the formula:

```
                                              (SEQ ID NO: 7)
H-Ser-Tyr-Ser-Met-Glu-His-Phe-Arg-Trp-Gly-
    1   2   3   4   5   6   7   8   9  10

Lys-Pro-Val-Gly-Lys-Lys-Arg
 11  12  13  14  15  16  17
``` or a fragment, complex, aggregate, or analog thereof, or any combination thereof.

In some embodiments, the ACTH peptide or fragment, analog, complex or aggregate thereof, or any combination thereof, is a fragment peptide chosen from the group of:

```
                                              (SEQ ID NO: 6)
H-Ser-Tyr-Ser-Met-Glu-His-Phe-Arg-Trp-Gly-
    1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro
 21  22 23   24
and
                                              (SEQ ID NO: 7)
H-Ser-Tyr-Ser-Met-Glu-His-Phe-Arg-Trp-Gly-
Lys-Pro-Val-Gly-Lys-Lys-Arg;
``` or a complex, aggregate, pharmaceutically acceptable salt, C-terminal ester or amide or N-terminal acetylation thereof, or any combination thereof.

In some embodiments, the ACTH peptide or fragment, analog, complex or aggregate thereof, or any combination thereof is a peptide of 17-20 amino acids, 21-25 amino acids, 26-30 amino acids, 31-35 amino acids, 36-40 amino acids, or 40-45 amino acids.

In some embodiments, the ACTH peptide or fragment, analog, complex or aggregate thereof, or any combination thereof is a peptide with about 50%, 60%, 70%, 80%, 90%, or 100% homology to ACTH. In some embodiments the homologous substitutions are conservative substitutions.

In some embodiments, the ACTH peptide or fragment, analog, complex or aggregate thereof, or any combination thereof, is administered as an ACTH formulation. In some embodiments, the ACTH peptide or fragment, analog, complex or aggregate thereof, or any combination thereof, is administered as ACTHAR® (adrenocorticotropic hormone) gel. In some embodiments, the ACTH peptide or fragment, analog, complex or aggregate thereof, or any combination thereof, is formulated as an aerosol, nasal spray, syrup, tablet, mini-tablet, capsule, pill, fast-melt strip, transdermal patch, cream, gel, ointment, solid, liquid solution, emulsion, suspension, powder, injectable solution, intravenous drip, aqueous liquid dispersion, self-emulsifying dispersion, solid solution, liposomal dispersion, immediate release formulation, prodrug, prolonged release formulation, controlled release formulation, fast melt formulation, delayed release formulation, pulsatile release formulation, multiparticulate formulation or mixed immediate and controlled release formulation. In some embodiments, the ACTH peptide or fragment, analog, complex or aggregate thereof, or any combination thereof, is administered as a prodrug. In some embodiments, the ACTH peptide or fragment, analog, complex or aggregate thereof, or any combination thereof, is administered as a prolonged release formulation. In some embodiments, the ACTH peptide or fragment, analog, complex or aggregate thereof, or any combination thereof, is administered as a nasal spray. In some embodiments, the ACTH peptide or fragment, analog, complex or aggregate thereof, or any combination thereof, is formulated as a gel.

In some embodiments, the ACTH peptide or fragment, analog, complex or aggregate thereof, or any combination thereof, is administered intramuscularly, subcutaneously, intravenously, intrathecally, orally, systemically, topically, transmucosally, parenterally, intranasally, buccally, or transdermally, rectally, by inhalation or by implant. In some embodiments, the ACTH peptide or fragment, analog, complex or aggregate thereof, or any combination thereof, is administered parenterally. In some embodiments, the ACTH peptide or fragment, analog, complex or aggregate thereof, or any combination thereof, is administered intramuscularly. In some embodiments, the ACTH peptide or fragment, analog, complex or aggregate thereof, or any combination thereof, is administered by injection intramuscularly. In some embodiments, the ACTH peptide or fragment, analog, complex or aggregate thereof, or any combination thereof, is administered subcutaneously. In some embodiments, the ACTH peptide or fragment, analog, complex or aggregate thereof, or any combination thereof, is administered by injection subcutaneously. In some embodiments, the ACTH peptide or fragment, analog, complex or aggregate thereof, or any combination thereof, is administered intravenously. In some embodiments, the ACTH peptide or fragment, analog, complex or aggregate thereof, or any combination thereof, is administered intrathecally. In some embodiments, the ACTH peptide or fragment, analog, complex or aggregate thereof, or any combination thereof, is administered as an implant. In some embodiments, the ACTH peptide or fragment, analog, complex or aggregate thereof, or any combination thereof, is administered via an erodible implant.

In some embodiments, the ACTH peptide or fragment, analog, complex or aggregate thereof, or any combination thereof, is a porcine, human, bovine, sheep, rabbit, chicken, goat or recombinant ACTH peptide or fragment, analog, complex or aggregate thereof, or any combination thereof. In some embodiments, the ACTH peptide or fragment, analog, complex or aggregate thereof, or any combination thereof, is a porcine ACTH peptide or fragment, analog, complex or aggregate thereof, or any combination thereof. In some embodiments, the ACTH peptide or fragment, analog, complex or aggregate thereof, or any combination thereof, is a recombinant ACTH peptide or fragment, analog, complex or aggregate thereof, or any combination thereof. In some embodiments, the ACTH peptide or fragment, analog, complex or aggregate thereof, or any combination thereof, is a recombinant human ACTH peptide or fragment, analog, complex or aggregate thereof, or any combination thereof. In some embodiments, the ACTH peptide or fragment, analog, complex or aggregate thereof, or any combination thereof, is a synthetic ACTH peptide or fragment, analog, complex or aggregate thereof, or any combination thereof, including herein solid phase support sequential synthesis. In some embodiments, the ACTH peptide or fragment, analog, complex or aggregate thereof, or any combination thereof, is a synthetic human ACTH peptide or fragment, analog, complex or aggregate thereof, or any combination thereof. In some embodiments, the ACTH peptide or fragment, analog, complex or aggregate thereof, or any combination thereof, is a porcine-derived ACTH peptide or fragment, analog, complex or aggregate thereof, or any combination thereof.

In some embodiments, the methods provided herein further comprise administration of a second therapeutic treatment. In certain embodiments, the second therapeutic treatment is administered sequentially or simultaneously or in staggered sequences.

In certain embodiments, the second therapeutic treatment is mechanical ventilation, a glucocorticoid, a surfactant, inhaled nitric oxide, an antioxidant, a protease inhibitor, a recombinant human activated protein C, a β2-agonist, lisofylline, a statin, inhaled heparin, a diuretic, a sedative, an analgesic, a muscle relaxant, an antibiotic, inhaled prostacyclin, inhaled synthetic prostacyclin analog, ketoconazole, alprostadil, keratinocyte growth factor, beta-agonists, human monoclonal antibody (mAb) against TS factor 7a (tissue factor VIIa), interferon receptor agonists, insulin, perfluorocarbon, budesonide, recombinant human angiotensin-converting enzyme (ACE), recombinant human Clara cell 10 kDa (CC10) protein, tissue plasminogen activator, human mesenchymal stem cells, nutritional therapy and extracorporeal membrane oxygenation (ECOM).

In certain embodiments, the second therapeutic treatment is a glucocorticoid, such as, for example, methylprednisolone, dexamethasone, prednisone, prednisolone, betamethasone, triamcinolone, triamcinolone acetonide, budesonide, and beclometasone; beta-agonists, such as, for example, albuterol; lisofylline; rosuvastatin, inhaled heparin; inhaled nitric oxide; recombinant human activated protein C; NSAIDS, such as, for example, ibuprofen; naproxen, and acetaminophen; cisatracurium besylate; procysteine; acetylcysteine; inhaled prostacyclin; ketoconazole; alprostadil; keratinocyte growth factor; human mAb against TS factor 7a; insulin; perfluorocarbons, recombinant human ACE; recombinant human CC10 protein; tissue plasminogen activator; human mesenchymal stem cells; or nutritional therapy such as a combination of omega-3 fatty acids, antioxidants, and γ-linolenic acids with isocaloric foods and extracorporeal membrane oxygenation (ECMO).

In some embodiments, ARDS is mild to moderate ARDS or moderate to severe ARDS. In certain embodiments, ARDS is mild ARDS. In certain embodiments ARDS is moderate ARDS. In certain embodiments, ARDS is severe ARDS. Clinical measurements of disease severity and rankings made from those measurements are known in the medical literature, some of which are noted herein. There are also known biological markers of disease severity and outcome prognosis that are useful in treating the disease and stratifying patients for treatment. See for example, Johnson, et al. (2010), especially Table 1.

In some embodiments, provided herein is a method of preventing or treating an individual diagnosed with, suspected of having, or at risk for developing ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof is administered as a first dose and one or more subsequent doses.

In some embodiments, provided herein is a method of preventing or treating an individual diagnosed with or suspected of having, or at risk of developing ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof, is a $ACTH_{1-39}$ peptide having the formula:

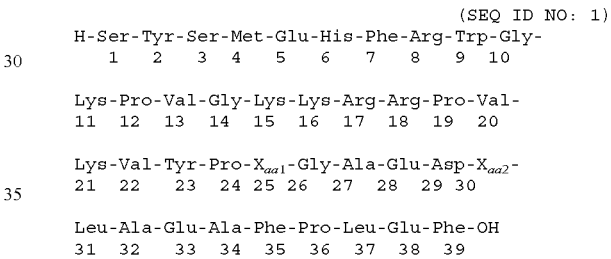

```
                                              (SEQ ID NO: 1)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24  25   26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof, wherein $X_{aa1}$ is Asp or Asn; and $X_{aa2}$ is Gln or Glu.

In some embodiments, provided herein is a method of preventing or treating an individual diagnosed with, suspected of having, or at risk for developing ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof, is a $ACTH_{1-39}$ peptide having the formula:

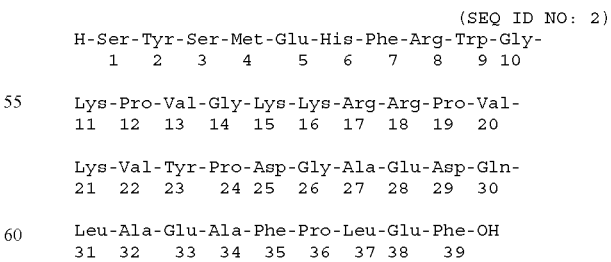

```
                                              (SEQ ID NO: 2)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23   24  25  26  27  28  29  30

Leu-Ala-Glu-Ala-Phe-Pro-Leu-Glu-Phe-OH
 31  32  33  34  35  36  37 38  39
``` or a fragment, complex, aggregate, or analog thereof, or any combination thereof.

In some embodiments, provided herein is a method of preventing or treating an individual diagnosed with, suspected of having, or at risk for developing ARDS comprising administration of adrenocorticotropic hormone (ACTH)

peptide, or fragment, analog, complex or aggregate thereof, or any combination thereof, to an individual in need thereof, wherein the ACTH peptide or fragment, analog, complex or aggregate thereof, or any combination thereof, is a ACTH$_{1-39}$ peptide having the formula:

```
                                              (SEQ ID NO: 3)
H-Ser-Tyr-Ser-Met-Glu-His-Phe-Arg-Trp-Gly-
   1    2    3    4    5    6    7    8    9   10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof, is a ACTH$_{1-39}$ peptide having the formula:

```
                                              (SEQ ID NO: 4)
H-Ser-Tyr-Ser-Met-Glu-His-Phe-Arg-Trp-Gly-
   1    2    3    4    5    6    7    8    9   10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof, is a ACTH$_{1-39}$ peptide having the formula:

```
                                              (SEQ ID NO: 5)
H-Ser-Tyr-Ser-Met-Glu-His-Phe-Arg-Trp-Gly-
   1    2    3    4    5    6    7    8    9   10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing ARDS comprising administration of an ACTH peptide or fragment, analog, complex or aggregate thereof, or any combination thereof, wherein the ACTH peptide or fragment, analog, complex or aggregate thereof, or any combination thereof, is a ACTH$_{1-39}$ peptide having the formula:

```
                                              (SEQ ID NO: 1)
H-Ser-Tyr-Ser-Met-Glu-His-Phe-Arg-Trp-Gly-
   1    2    3    4    5    6    7    8    9   10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24  25   26  27  28  29  30

Leu-Ala-Glu-Ala-Phe-Pro-Leu-Glu-Phe-OH
 31  32  33  34  35  36  37  38  39
``` as a first dose and one or more subsequent doses, wherein $X_{aa1}$ is Asp or Asn; and $X_{aa2}$ is Gln or Glu.

In some embodiments, provided herein is a method of preventing or treating an individual diagnosed with, suspected of having, or at risk for developing ARDS comprising administration of an ACTH peptide or fragment, analog, complex or aggregate thereof, or any combination thereof, wherein the ACTH peptide or fragment, analog, complex or aggregate thereof, or any combination thereof, is a ACTH$_{1-39}$ peptide having the formula:

```
                                              (SEQ ID NO: 2)
H-Ser-Tyr-Ser-Met-Glu-His-Phe-Arg-Trp-Gly-
   1    2    3    4    5    6    7    8    9   10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing ARDS comprising administration of an ACTH peptide or fragment, analog, complex or aggregate thereof, or any combination thereof, wherein the ACTH peptide or fragment, analog, complex or aggregate thereof, or any combination thereof, is a ACTH$_{1-39}$ peptide having the formula:

```
                                              (SEQ ID NO: 3)
H-Ser-Tyr-Ser-Met-Glu-His-Phe-Arg-Trp-Gly-
   1    2    3    4    5    6    7    8    9   10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing ARDS comprising administration of an ACTH peptide or fragment, analog, complex or aggregate thereof, or any combination thereof, wherein the ACTH peptide or fragment, analog, complex or aggregate thereof, or any combination thereof, is a ACTH$_{1-39}$ peptide having the formula:

```
                                              (SEQ ID NO: 4)
    H-Ser-Tyr-Ser-Met-Glu-His-Phe-Arg-Trp-Gly-
       1   2   3   4   5   6   7   8   9  10

Lys-Pro-Val-Gly-Lys-Lys-Arg-Arg-Pro-Val-
     11  12  13  14  15  16  17  18  19  20

Lys-Val-Tyr-Pro-Asp-Gly-Ala-Glu-Asp-Glu-
     21  22  23  24  25  26  27  28  29  30

Leu-Ala-Glu-Ala-Phe-Pro-Leu-Glu-Phe-OH
     31  32  33  34  35  36  37  38  39
``` as a first dose and one or more subsequent doses.

In some embodiments, provided herein is a method of preventing or treating an individual diagnosed with, suspected of having, or at risk for developing ARDS comprising administration of an ACTH peptide or fragment, analog, complex or aggregate thereof, or any combination thereof, wherein the ACTH peptide or fragment, analog, complex or aggregate thereof, or any combination thereof, is a ACTH$_{1-39}$ peptide having the formula:

```
                                              (SEQ ID NO: 5)
    H-Ser-Tyr-Ser-Met-Glu-His-Phe-Arg-Trp-Gly-
       1   2   3   4   5   6   7   8   9  10

Lys-Pro-Val-Gly-Lys-Lys-Arg-Arg-Pro-Val-
     11  12  13  14  15  16  17  18  19  20

Lys-Val-Tyr-Pro-Asn-Gly-Ala-Glu-Asp-Gln-
     21  22  23  24  25  26  27  28  29  30

Leu-Ala-Glu-Ala-Phe-Pro-Leu-Glu-Phe-OH
     31  32  33  34  35  36  37  38  39
``` as a first dose and one or more subsequent doses.

In some embodiments, provided herein is a method of preventing or treating an individual diagnosed with, suspected of having, or at risk for developing ARDS comprising administration of an ACTH peptide or fragment, analog, complex or aggregate thereof, or any combination thereof as a first and one or more subsequent doses, wherein the first dose of ACTH peptide or fragment, analog, complex or aggregate thereof, or any combination thereof is between about 10 U and about 150 U, and the one or more subsequent doses of ACTH peptide or fragment, analog, complex or aggregate thereof, or any combination thereof, are between about 20% and about 80% of the first dose. In further embodiments, the methods described herein comprise administration of an ACTH peptide or fragment, analog, complex or aggregate thereof, or any combination thereof as a first and one or more subsequent doses, wherein the first dose of ACTH peptide or fragment, analog, complex or aggregate thereof, or any combination thereof is about 80 U, and the one or more subsequent doses of ACTH peptide or fragment, analog, complex or aggregate thereof, or any combination thereof is about 40 U.

In some embodiments, provided herein is a method of preventing or treating an individual diagnosed with, suspected of having, or at risk for developing ARDS comprising administration of an ACTH$_{1-39}$ peptide or fragment, analog, complex or aggregate thereof, or any combination thereof, having the formula:

```
                                              (SEQ ID NO: 1)
    H-Ser-Tyr-Ser-Met-Glu-His-Phe-Arg-Trp-Gly-
       1   2   3   4   5   6   7   8   9  10

Lys-Pro-Val-Gly-Lys-Lys-Arg-Arg-Pro-Val-
     11  12  13  14  15  16  17  18  19  20

Lys-Val-Tyr-Pro-X_{aa1}-Gly-Ala-Glu-Asp-X_{aa2}-
     21  22  23  24  25  26  27  28  29  30

Leu-Ala-Glu-Ala-Phe-Pro-Leu-Glu-Phe-OH
     31  32  33  34  35  36  37  38  39
``` wherein $X_{aa1}$ is Asp or Asn; and $X_{aa2}$ is Gln or Glu, as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing ARDS comprising administration of an ACTH$_{1-39}$ peptide or fragment, analog, complex or aggregate thereof, or any combination thereof, having the formula:

```
                                              (SEQ ID NO: 2)
    H-Ser-Tyr-Ser-Met-Glu-His-Phe-Arg-Trp-Gly-
       1   2   3   4   5   6   7   8   9  10

Lys-Pro-Val-Gly-Lys-Lys-Arg-Arg-Pro-Val-
     11  12  13  14  15  16  17  18  19  20

Lys-Val-Tyr-Pro-Asp-Gly-Ala-Glu-Asp-Gln-
     21  22  23  24  25  26  27  28  29  30

Leu-Ala-Glu-Ala-Phe-Pro-Leu-Glu-Phe-OH
     31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing ARDS comprising administration of an ACTH$_{1-39}$ peptide or fragment, analog, complex or aggregate thereof, or any combination thereof, having the formula:

```
                                              (SEQ ID NO: 3)
    H-Ser-Tyr-Ser-Met-Glu-His-Phe-Arg-Trp-Gly-
       1   2   3   4   5   6   7   8   9  10

Lys-Pro-Val-Gly-Lys-Lys-Arg-Arg-Pro-Val-
     11  12  13  14  15  16  17  18  19  20

Lys-Val-Tyr-Pro-Asn-Gly-Ala-Glu-Asp-Glu-
     21  22  23  24  25  26  27  28  29  30

Leu-Ala-Glu-Ala-Phe-Pro-Leu-Glu-Phe-OH
     31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing ARDS comprising administration of an ACTH$_{1-39}$ peptide or fragment, analog, complex or aggregate thereof, or any combination thereof, having the formula:

```
                                              (SEQ ID NO: 4)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing ARDS comprising administration of an $ACTH_{1-39}$ peptide or fragment, analog, complex or aggregate thereof, or any combination thereof, having the formula:

```
                                              (SEQ ID NO: 5)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing moderate to severe ARDS comprising administration of adrenocorticotropic hormone (ACTH) peptide, or fragment, analog, complex or aggregate thereof, or any combination thereof, to an individual in need thereof.

In certain embodiments, the ACTH peptide or fragment, analog, complex or aggregate thereof, or any combination thereof, is administered as a first dose and one or more subsequent doses.

In some embodiments, provided herein is a method of preventing or treating an individual diagnosed with, suspected of having, or at risk for developing moderate to severe ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof is administered as a first dose and one or more subsequent doses.

In some embodiments, provided herein is the use of adrenocorticotropic hormone (ACTH) peptide, or fragment, analog, complex or aggregate thereof, or any combination thereof for treating an individual diagnosed with, suspected of having, or at risk for developing moderate to severe ARDS wherein the ACTH peptide or fragment, analog, complex or aggregate thereof, or any combination thereof, is administered as a first dose and one or more subsequent doses.

In some embodiments, provided herein is a method of preventing or treating an individual diagnosed with, suspected of having, or at risk for developing moderate to severe ARDS comprising administration of an ACTH peptide or fragment, analog, complex or aggregate thereof, or any combination thereof, wherein the ACTH is a $ACTH_{1-39}$ peptide having the formula:

```
                                              (SEQ ID NO: 1)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_aa1-Gly-Ala-Glu-Asp-X_aa2-
 21  22  23  24  25   26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof, wherein $X_{aa1}$ is Asp or Asn; and $X_{aa2}$ is Gln or Glu.

In some embodiments, provided herein is a method of preventing or treating an individual diagnosed with, suspected of having, or at risk for developing moderate to severe ARDS comprising administration of an ACTH peptide or fragment, analog, complex or aggregate thereof, or any combination thereof, wherein the ACTH is a $ACTH_{1-39}$ peptide having the formula:

```
                                              (SEQ ID NO: 2)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing moderate to severe ARDS comprising administration of an ACTH peptide or fragment, analog, complex or aggregate thereof, or any combination thereof, wherein the ACTH is a $ACTH_{1-39}$ peptide having the formula:

```
                                              (SEQ ID NO: 3)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing moderate to severe ARDS comprising administration of an ACTH peptide or fragment, analog, complex or aggregate thereof, or any combination thereof, wherein the ACTH is a $ACTH_{1-39}$ peptide having the formula:

```
                                              (SEQ ID NO: 4)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24 25   26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing moderate to severe ARDS comprising administration of an ACTH peptide or fragment, analog, complex or aggregate thereof, or any combination thereof, wherein the ACTH is a $ACTH_{1-39}$ peptide having the formula:

```
                                              (SEQ ID NO: 5)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24 25   26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing moderate to severe ARDS comprising administration of an $ACTH_{1-39}$ peptide, fragment, analog, complex or aggregate thereof, or any combination thereof, having the formula:

```
                                              (SEQ ID NO: 1)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24 25      26  27  28  29  30

Leu-Ala-Glu-Ala-Phe-Pro-Leu-Glu-Phe-OH
 31  32  33  34  35  36  37  38  39
``` as a first dose and one or more subsequent doses, wherein $X_{aa1}$ is Asp or Asn; and $X_{aa2}$ is Gln or Glu.

In some embodiments, provided herein is a method of preventing or treating an individual diagnosed with, suspected of having, or at risk for developing moderate to severe ARDS comprising administration of an $ACTH_{1-39}$ peptide, fragment, analog, complex or aggregate thereof, or any combination thereof, having the formula:

```
                                              (SEQ ID NO: 2)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24   25   26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing moderate to severe ARDS comprising administration of an $ACTH_{1-39}$ peptide, fragment, analog, complex or aggregate thereof, or any combination thereof, having the formula:

```
                                              (SEQ ID NO: 3)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24 25   26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing moderate to severe ARDS comprising administration of an $ACTH_{1-39}$ peptide, fragment, analog, complex or aggregate thereof, or any combination thereof, having the formula:

```
                                              (SEQ ID NO: 4)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23  24 25   26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing moderate to severe ARDS comprising administration of an $ACTH_{1-39}$ peptide, fragment, analog, complex or aggregate thereof, or any combination thereof, having the formula:

```
                                              (SEQ ID NO: 5)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24 25   26  27  28  29  30
```

-continued
Leu-Ala-Glu-Ala-Phe-Pro-Leu-Glu-Phe-OH
31  32  33  34  35  36  37  38  39 as a first dose and one or more subsequent doses.

In some embodiments, provided herein is a method of preventing or treating an individual diagnosed with, suspected of having, or at risk for developing moderate to severe ARDS comprising administration of an ACTH peptide or fragment, analog, complex or aggregate thereof, or any combination thereof as a first and one or more subsequent doses, wherein the first dose of ACTH peptide or fragment, analog, complex or aggregate thereof, or any combination thereof is between about 10 U and about 150 U, and the one or more subsequent doses of ACTH peptide or fragment, analog, complex or aggregate thereof, or any combination thereof are between about 20% and about 80% of the first dose.

In some embodiments, provided herein is a method of preventing or treating an individual diagnosed with, suspected of having, or at risk for developing moderate to severe ARDS comprising administration of an $ACTH_{1-39}$ peptide or fragment, analog, complex or aggregate thereof, or any combination thereof, having the formula:

```
                                         (SEQ ID NO: 1)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24  25    26  27  28  29  30

Leu-Ala-Glu-Ala-Phe-Pro-Leu-Glu-Phe-OH
 31  32  33  34  35  36  37  38  39
``` wherein $X_{aa1}$ is Asp or Asn; and $X_{aa2}$ is Gln or Glu, as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing moderate to severe ARDS comprising administration of an $ACTH_{1-39}$ peptide or fragment, analog, complex or aggregate thereof, or any combination thereof, having the formula:

```
                                         (SEQ ID NO: 2)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing moderate to severe ARDS comprising administration of an $ACTH_{1-39}$ peptide or fragment, analog, complex or aggregate thereof, or any combination thereof, having the formula:

```
                                         (SEQ ID NO: 3)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing moderate to severe ARDS comprising administration of an $ACTH_{1-39}$ peptide or fragment, analog, complex or aggregate thereof, or any combination thereof, having the formula:

```
                                         (SEQ ID NO: 4)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing moderate to severe ARDS comprising administration of an $ACTH_{1-39}$ peptide or fragment, analog, complex or aggregate thereof, or any combination thereof, having the formula:

```
                                         (SEQ ID NO: 5)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing mild to moderate ARDS comprising administration of adrenocorticotropic hormone (ACTH) peptide, or fragment, analog, complex or aggregate thereof, or any combination thereof, to an individual in need thereof.

In certain embodiments, the ACTH peptide or fragment, analog, complex or aggregate thereof, or any combination thereof, is administered as a first dose and one or more subsequent doses.

In some embodiments, provided herein is a method of preventing or treating an individual diagnosed with, suspected of having, or at risk for developing mild to moderate ARDS comprising administration of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof is administered as a first dose and one or more subsequent doses.

In some embodiments, provided herein is the use of adrenocorticotropic hormone (ACTH) peptide, or fragment, analog, complex or aggregate thereof, or any combination thereof for treating an individual diagnosed with, suspected of having, or at risk for developing mild to moderate ARDS wherein the ACTH peptide or fragment, analog, complex or aggregate thereof, or any combination thereof, is administered as a first dose and one or more subsequent doses.

In some embodiments, provided herein is a method of preventing or treating an individual diagnosed with, suspected of having, or at risk for developing mild to moderate ARDS comprising administration of an ACTH peptide or fragment, analog, complex or aggregate thereof, or any combination thereof, wherein the ACTH is a $ACTH_{1-39}$ peptide having the formula:

```
                                         (SEQ ID NO: 1)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24  25   26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof, wherein $X_{aa1}$ is Asp or Asn; and $X_{aa2}$ is Gln or Glu.

In some embodiments, provided herein is a method of preventing or treating an individual diagnosed with, suspected of having, or at risk for developing mild to moderate ARDS comprising administration of an ACTH peptide or fragment, analog, complex or aggregate thereof, or any combination thereof, wherein the ACTH is a $ACTH_{1-39}$ peptide having the formula:

```
                                         (SEQ ID NO: 2)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing mild to moderate ARDS comprising administration of an ACTH peptide or fragment, analog, complex or aggregate thereof, or any combination thereof, wherein the ACTH is a $ACTH_{1-39}$ peptide having the formula:

```
                                         (SEQ ID NO: 3)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing moderate ARDS comprising administration of an ACTH peptide or fragment, analog, complex or aggregate thereof, or any combination thereof, wherein the ACTH is a $ACTH_{1-39}$ peptide having the formula:

```
                                         (SEQ ID NO: 4)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing mild to moderate ARDS comprising administration of an ACTH peptide or fragment, analog, complex or aggregate thereof, or any combination thereof, wherein the ACTH is a $ACTH_{1-39}$ peptide having the formula:

```
                                         (SEQ ID NO: 5)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` or a fragment, complex, aggregate, or analog thereof, or any combination thereof.

In some embodiments, provided herein is a method of preventing or treating an individual diagnosed with, suspected of having, or at risk for developing mild to moderate ARDS comprising administration of an $ACTH_{1-39}$ peptide, fragment, analog, complex or aggregate thereof, or any combination thereof, having the formula:

```
                                    (SEQ ID NO: 1)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24   25    26  27  28  29  30

Leu-Ala-Glu-Ala-Phe-Pro-Leu-Glu-Phe-OH
 31  32  33  34  35  36  37  38  39
```

As a first dose and one or more subsequent doses, wherein $X_{aa1}$ is Asp or Asn; and $X_{aa2}$ is Gln or Glu.

In some embodiments, provided herein is a method of preventing or treating an individual diagnosed with, suspected of having, or at risk for developing mild to moderate ARDS comprising administration of an $ACTH_{1-39}$ peptide, fragment, analog, complex or aggregate thereof, or any combination thereof, having the formula:

```
                                    (SEQ ID NO: 2)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing mild to moderate ARDS comprising administration of an $ACTH_{1-39}$ peptide, fragment, analog, complex or aggregate thereof, or any combination thereof, having the formula:

```
                                    (SEQ ID NO: 3)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing mild to moderate ARDS comprising administration of an $ACTH_{1-39}$ peptide, fragment, analog, complex or aggregate thereof, or any combination thereof, having the formula:

```
                                    (SEQ ID NO: 4)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20
```

-continued
```
Lys-Val-Tyr-Pro-Asp-Gly-Ala-Glu-Asp-Glu-
 21  22  23  24  25  26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing mild to moderate ARDS comprising administration of an $ACTH_{1-39}$ peptide, fragment, analog, complex or aggregate thereof, or any combination thereof, having the formula:

```
                                    (SEQ ID NO: 5)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39
``` as a first dose and one or more subsequent doses.

In some embodiments, provided herein is a method of preventing or treating an individual diagnosed with, suspected of having, or at risk for developing mild to moderate ARDS comprising administration of an ACTH peptide or fragment, analog, complex or aggregate thereof, or any combination thereof as a first and one or more subsequent doses, wherein the first dose of ACTH peptide or fragment, analog, complex or aggregate thereof, or any combination thereof is between about 10 U and about 150 U, and the one or more subsequent doses of ACTH peptide or fragment, analog, complex or aggregate thereof, or any combination thereof are between about 20% and about 80% of the first dose.

In some embodiments, provided herein is a method of preventing or treating an individual diagnosed with, suspected of having, or at risk for developing moderate ARDS comprising administration of an $ACTH_{1-39}$ peptide or fragment, analog, complex or aggregate thereof, or any combination thereof, having the formula:

```
                                    (SEQ ID NO: 1)
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23   24  25   26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose, and wherein $X_{aa1}$ is Asp or Asn; and $X_{aa2}$ is Gln or Glu.

In some embodiments, provided herein is a method of preventing or treating an individual diagnosed with, suspected of having, or at risk for developing mild to moderate ARDS comprising administration of an $ACTH_{1-39}$ peptide or fragment, analog, complex or aggregate thereof, or any combination thereof, having the formula:

```
                                          (SEQ ID NO: 2)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Gln-
 21  22  23   24 25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing mild to moderate ARDS comprising administration of an $ACTH_{1-39}$ peptide or fragment, analog, complex or aggregate thereof, or any combination thereof, having the formula:

```
                                          (SEQ ID NO: 3)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Glu-
 21  22  23   24 25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing mild to moderate ARDS comprising administration of an $ACTH_{1-39}$ peptide or fragment, analog, complex or aggregate thereof, or any combination thereof, having the formula:

```
                                          (SEQ ID NO: 4)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asp-Gly-Ala-Glu-Asp-Glu-
 21  22  23   24 25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method of preventing or treating an individual diagnosed with, suspected of having, or at risk for developing mild to moderate ARDS comprising administration of an $ACTH_{1-39}$ peptide or fragment, analog, complex or aggregate thereof, or any combination thereof, having the formula:

```
                                          (SEQ ID NO: 5)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-Asn-Gly-Ala-Glu-Asp-Gln-
 21  22  23   24 25  26  27  28  29  30

Leu-Ala-Glu-Ala-Phe-Pro-Leu-Glu-Phe-OH
 31  32  33  34  35  36  37  38  39
``` as a first and one or more subsequent doses, wherein the first dose is between about 10 U and about 150 U, and the one or more subsequent doses are between about 20% and about 80% of the first dose.

In some embodiments, provided herein is a method for increasing the safety of administering $ACTH_{1-39}$ or $ACTH_{1-24}$ or a combination thereof, to a severely ill patient comprising a first phase of dosing of about 4 to about 10 days duration wherein a patient receives a daily dose of 16-64 U daily or in a divided dose of 8-32 U administered at a selected interval within each day, followed by one or more subsequent phases of about 4 to about 10 days duration each wherein each successive phase of doses is about 50% of the dose of the preceding phase, followed by a final phase wherein the dose of the preceding phase in maintained and administered at intervals of every other day.

In some embodiments, provided herein is a method for increasing the safety of administering $ACTH_{1-39}$ or $ACTH_{1-24}$ or a combination thereof, to a severely ill patient comprising a first phase of dosing of about 7 days duration wherein the dose is administered as 64 U once per day or 32 U twice a day, followed by a second phase of about 7 days duration wherein the daily, or twice daily, dose is reduced by about 50%, followed by a third phase of about 7 days duration wherein the daily, or twice daily, dose of the second phase is reduced by about 50% and followed by a fourth phase of about 7 days, the dose of the third phase is administered every other day.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. The invention is better understood from the following detailed description when read in conjunction with the accompanying drawings. It is emphasized that according to common practice, the various features of the drawings are not to-scale. On the contrary, the dimensions of the various features are arbitrarily expanded or reduced for clarity. Included in the drawings are the following figures.

FIG. 6, described in Example 10, illustrates the effect of ACTHAR® (adrenocorticotropic hormone) on the number of animals with no abnormal clinical phenotype after LPS-induced acute lung injury.

DETAILED DESCRIPTION OF THE INVENTION

Figure 1:
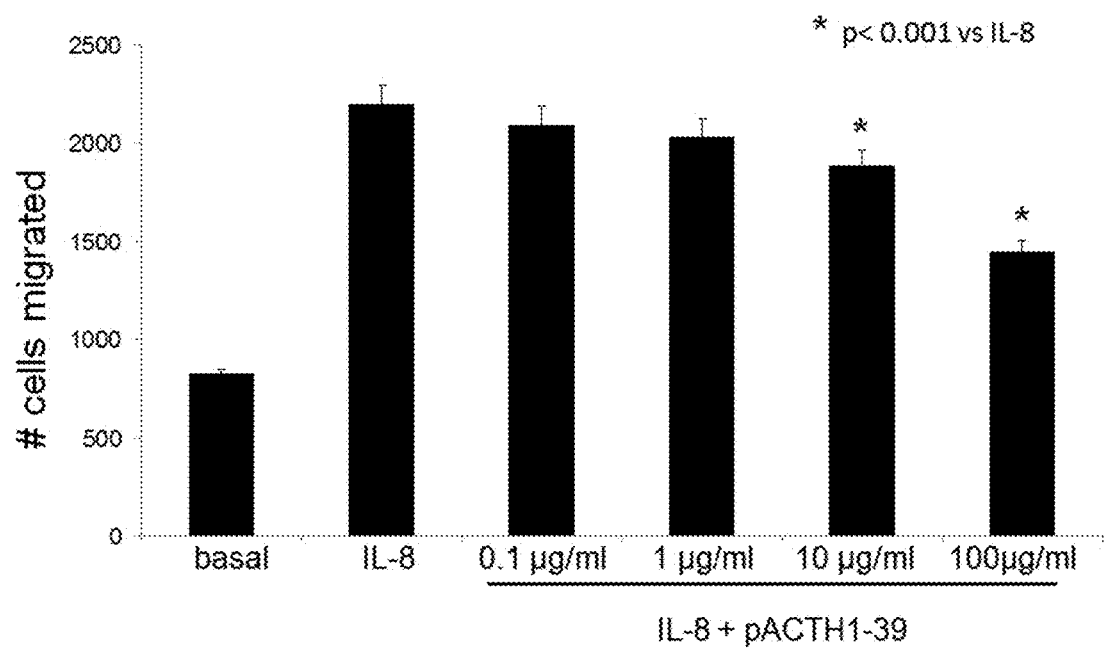
FIG. 1, described in Example 5, illustrates four concentrations of $pACTH_{1-39}$ (0.1, 1, 10, 100 µg/mL) tested in cells isolated from neutrophil donors in response to IL-8.

Provided herein, in some embodiments, are methods of treatment of acute respiratory distress syndrome (ARDS) comprising administration of ACTH to an individual in need thereof. Experimental and clinical evidence have shown a strong causal relationship between persistence of system inflammation and the progression of ARDS. Patients with unresolving ARDS typically have persistent elevation of both systemic and bronchoalveolar lavage levels of inflammatory mediators, fibrogenesis markers, and alveolar-capillary membrane permeability. Treatment of ARDS can be directed towards down-regulation of systemic inflammation and restoration of tissue homeostasis.

ACTH is a hormone that is secreted by the pituitary gland and is a part of the hypothalamus-pituitary-adrenal (HPA) axis that maintains the stress response and homeostasis in the body. As part of the HPA axis, ACTH stimulates the adrenal production of corticosteroids, which are well-acknowledged for their anti-inflammatory effect. Moreover, exogenous corticosteroid therapy can have beneficial effects on the suppression of systemic inflammation, gas exchange, and respiratory mechanics in patients with ARDS [Marik P E, Meduri G U, Rocco P R, Annane D. Glucocorticoid treatment in acute lung injury and acute respiratory distress syndrome. Crit Care Clin. 2011; 27(3):589-607; Meduri G U, Headley A S, Golden E, et al. Effect of prolonged methylprednisolone therapy in unresolving acute respiratory distress syndrome: A randomized controlled trial. JAMA. 1998; 280(2):159-165]. ACTH is also an important agonist in the melanocortin system, which has an integral role in homeostatic control of a variety of physiological functions, such as anti-inflammation and immunomodulation. ACTH$_{1-39}$ binds to and activates all five subtypes of melanocortin receptors with a different affinity and activation at each receptor. [Schiöth H B, Muceniece R, Wikberg J E S, Chhajlani V. Characterisation of melanocortin receptor subtypes by radioligand binding analysis. Eur J Pharmacol. 1995; 288(3):311-7]. Thus, modulation of levels of ACTH can have significant physiological implications.

Advantageously, in some embodiments, the methods of treatment of ARDS described herein comprise administration of adrenocorticotropic hormone (ACTH) to an individual in need thereof in doses and/or dosing regimens such that, for example, any dysregulation in pulmonary function is remedied or partially remedied, thereby alleviating the symptoms of ARDS. In some embodiments, the methods of treatment of ARDS described herein prevent, delay, reduce, or reverse damage to the lungs, thereby allowing for survival of individuals suspected of having, predisposed to, or at risk for developing ARDS. In certain embodiments, the doses and/or dosing regimens described herein are designed to minimize any abrupt shifts in ACTH levels in an individual (e.g., a surge, or a drop in levels of ACTH) and to moderate the steroidogenic effect on the adrenal medulla.

Acute Respiratory Distress Syndrome (ARDS)

Acute respiratory distress syndrome, or adult respiratory distress syndrome, is a type of severe acute lung dysfunction affecting all or most of both lungs and can be a severe complication of any number of factors such as pneumonia, sepsis, trauma, or inhaled irritants. The acute respiratory distress syndrome can be characterized by the influx of protein rich edema fluid into the air spaces due to increased permeability of the alveolar capillary barrier (Ware and Matthay 2000). Accumulation of neutrophils is often predominant in the pulmonary edema fluid and bronchoalveolar-lavage fluid of ARDS patients. The protein rich edema fluid in ARDS is typically due to accumulation of neutrophils, monocytes, denuded epithelial cells, and proinflammatory markers such as cytokines, proteases, oxidants, and procoagulant factors (Annual Rev. Pathol. Mech. Dis., 2011, 6, 147-163). Fluid build-up in the lungs leads to impaired gas exchange and occurs with concurrent systemic release of inflammatory mediators, causing inflammation, hypoxemia, and frequently multiple organ failure. Cytokines and other pro-inflammatory compounds can initiate and amplify the inflammatory response in ARDS. The acute respiratory distress syndrome, if not resolved completely in patients, can progress to fibrosing alveolitis with persistent hypoxemia, increased alveolar dead space, and a further decrease in pulmonary compliance. Multiple predisposing disorders as well as secondary factors including alcohol abuse, chronic lung disease, and low serum pH can substantially increase the risk of progression to acute respiratory distress syndrome. Complicating factors such as chronic liver disease, nonpulmonary organ dysfunction, sepsis, and advanced age can be used to predict the risk of death at the time of diagnosis of ARDS (Ware and Matthay 2000).

The Berlin Definition of ARDS partitions patients of ARDS by arterial partial pressure of oxygen to fraction of inspired oxygen ratio ($PaO_2/FiO_2$) into three levels of the syndrome: mild ARDS ($PaO_2/FiO_2$, 200-300), moderate ARDS ($PaO_2/FiO_2$=100-199), and severe ARDS ($PaO_2/FiO_2$<100). In addition, onset of ARDS is typically within one week of a known clinical insult or new or worsening respiratory symptoms; chest imaging typically include bilateral opacities not fully explained by effusions, lobar/lung collapse, or nodules; and the origin of edema typically is not fully explained by cardiac failure or fluid overload and is objectively evaluated (such as by echocardiography) if no clear predisposing factor for ARDS is present. In some embodiments, the methods of treatment of ARDS described herein are particularly suitable for the treatment of moderate or severe ARDS.

ARDS afflicts nearly 200,000 people in the United States each year, leading to approximately 75,000 deaths. Mechanical ventilation in an intensive care unit is the typical treatment. Supportive strategies, such as fluid management, sedation interruption, and early mobilization, are typically used as well. Patients who survive ARDS have increased risk of lower quality of life, pulmonary-disease specific health related quality of life, persistent cognitive impairment, and physical and psychological dysfunction. Examples of residual impairment of pulmonary mechanics and injury to the lung following ARDS include mild restriction, obstruction, impairment of the diffusing capacity of carbon monoxide, or gas exchange abnormalities with exercise.

ACTH

ACTH is a 39 amino acid peptide hormone secreted by the anterior pituitary gland. ACTH is secreted from the anterior pituitary in response to corticotropin-releasing hormone (CRH) that is secreted from the hypothalamus. The release of ACTH stimulates melanocortin receptors in the adrenal cortex with subsequent increased production of glucocorticosteroids and/or cortisol from the adrenal cortex, as well as binding to other melanocortin receptor subtypes.

ACTH is synthesized from a precursor polypeptide pre-pro-opiomelanocortin (pre-POMC). The removal of the signal peptide during translation produces a 267 amino acid polypeptide POMC. POMC undergoes a series of post-translational modifications to yield various polypeptide fragments including and not limited to ACTH, β-lipotropin, γ-lipotropin, α, β, γ-Melanocyte Stimulating Hormone (MSH) and β-endorphin. POMC, ACTH and β-lipotropin are also secreted from the pituitary gland in response to the hormone corticotropin-releasing hormone (CRH). Without being bound to any one particular theory, it is believed that ACTH (e.g, $ACTH_{1-39}$ or ACTHAR®) or fragments thereof, such as for example, $ACTH_{1-24}$ (SYNACTHEN®; tetracosactide) or $ACTH_{1-20}$, can be advantageous in the methods described herein due to the ability to induce a steroidogenic or a partial steroidogenic effect, depending on the peptide chosen and on the dosage regimen. In some embodiments, multiple hypothalamic, pituitary, and peripheral factors regulate stress-mediated or inflammation-induced POMC expression and/or ACTH secretion. Essential cellular functions maintaining metabolic and neuroendocrine control require a homeostatic, non-stressed pattern of ACTH and glucocorticoid secretion. ACTH secretion is characterized by both circadian periodicity and ultradian pulsatility that is generated by CRH release and is also influenced by peripheral corticosteroids. Thus, ACTH secretion peaks at about before 7 am and nadir adrenal steroid secretion occurs between about 11 pm and 3 am, with periodic secretory bursts occurring throughout the day. Serum cortisol levels also exhibit a similar pattern of circadian periodicity. These rhythms are further reinforced by visual cues and the light-dark cycle. In some instances, stress results in increased ACTH pulse amplitude. In some cases stress may be associated with loss of the diurnal rhythms.

In some instances, an abnormality in ACTH levels is associated with inflammation (e.g., increased release of pro-inflammatory cytokines). In some instances, an abnormality in ACTH levels is associated with reduced VEGF secretion. In some instances, reduced VEGF secretion is associated with reduced growth of new blood vessels and inadequate oxygen supply to tissues (e.g., neurons and/or muscles).

Definitions

For the purpose of interpreting this specification, the following definitions will apply. In the event that any definition set forth below conflicts with the usage of that word in any other document, including any document incorporated herein by reference, the definition set forth below shall always control for purposes of interpreting this specification and its associated claims unless a contrary meaning is clearly intended (for example by reference to a document where the term is originally used). Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as" also is not intended to be limiting. For example, the term "including" shall mean "including, but not limited to."

The term "ACTH" refers to corticotropin, adrenocorticotropic hormone, Tetracosactide or the like. The term "ACTH" also includes, but is not limited to, any ACTH peptide or any ACTH preparation as described herein. In some embodiments, ACTH is an ACTH peptide. As used herein, in some embodiments, "ACTH peptide" refers to $ACTH_{1-39}$ peptide of structure:

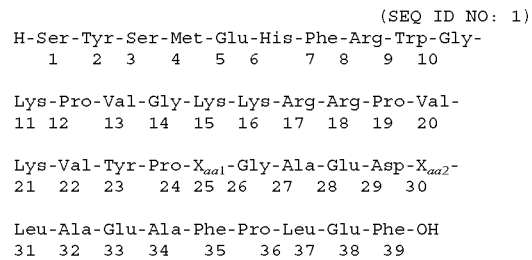

or any homologs, analogs, fragments, complexes or aggregates thereof, wherein $X_{aa1}$ is Asp or Asn; and $X_{aa2}$ is Gln or Glu. The term ACTH includes peptides or peptide fragments, complexes, salts or aggregates with about 40%, about 45%, about 50%, about 55%, about 60%, about 65%, about 70%, about 75%, about 80%, about 85%, about 90%, or about 95% homology with $ACTH_{1-39}$. The term ACTH includes ACTH from any source including human ACTH, mouse ACTH, rat ACTH, porcine ACTH, sheep ACTH, bovine ACTH, rabbit ACTH or any other source of ACTH.

In some embodiments, the ACTH peptide or fragment, analog, complex, or aggregate thereof, or any combination thereof, is a porcine ACTH peptide or fragment, analog, complex, or aggregate thereof; a human ACTH peptide or fragment, analog, complex, or aggregate thereof; or a recombinant ACTH peptide or fragment, analog, complex, or aggregate thereof. In some embodiments, the ACTH peptide is a porcine ACTH peptide, a human ACTH peptide, or a recombinant ACTH peptide. In some embodiments, the ACTH peptide is a porcine ACTH peptide. In some embodiments, the ACTH peptide is a human ACTH peptide. In some embodiments, the ACTH peptide is a recombinant ACTH peptide. In some embodiments, the ACTH peptide is a recombinant human ACTH peptide.

In some embodiments, ACTH is an ACTH preparation. As used herein, "ACTH preparation" refers to a mixture containing ACTH peptide and/or other peptide fragments and/or other proteins and/or other substances that together form a composition that is suitable for any methods and/or dosing regimen described herein. In some of such embodiments, ACTH is obtained from a homogenized pituitary extract of an appropriate animal (e.g., pituitary extract of a pig). Any suitable method is used to obtain a homogenized pituitary extract. In some of such embodiments, a homogenized pituitary extract includes ACTH peptide and/or other peptide fragments and/or other proteins and/or other substances that are contemplated as being part of the ACTH preparation that is compatible with any method described herein.

The term ACTH includes humanized and/or recombinant forms of ACTH and synthetic forms of ACTH. The term ACTH includes fragments of $ACTH_{1-39}$. Examples of synthetic forms and/or fragments of ACTH include and are not limited to $ACTH_{1-24}$ peptide having the formula (e.g., having the sequence of the following) and also known as tetracosactide or SYNACTHEN®:

```
                                          (SEQ ID NO: 6)
    H-Ser-Tyr-Ser-Met-Glu-His-Phe-Arg-Trp-Gly-
      1   2   3   4   5   6   7   8   9  10

Lys-Pro-Val-Gly-Lys-Lys-Arg-Arg-Pro-Val-
    11  12  13  14  15  16  17  18  19  20

Lys-Val-Tyr-Pro
    21  22  23  24
```

The term ACTH peptide, fragment, or analog does not include a peptide of formula (e.g., having the sequence of the following):

```
                                          (SEQ ID NO: 8)
    Ac-Ser-Tyr-Ser-Met-Glu-His-Phe-Arg-Trp-Gly-Lys-

Pro-Val-NH2
```

NO: 8) which is known as alpha-MSH or an analog thereof, or a peptide fragment of formula (e.g., having the sequence of the following):

```
                                          (SEQ ID NO: 9)
    H-Ser-Tyr-Ser-Met-Glu-His-Phe-Arg-Trp-Gly-Lys-

Pro-Val
``` or an analog thereof, or any combination thereof.

The term ACTH also includes synthetic preparations of ACTH that are commercially available including and not limited to ACTHAR® (adrenocorticotropic hormone) powder for injection or gel, SYNACTHEN® (tetracosactide), ADRENOMONE® (veterinary adrenocorticotropic hormone compositions), or the like. ACTHAR® (adrenocorticotropic hormone) is derived from porcine pituitary glands and the ACTH obtained therefrom includes one or more of the ACTH peptides of SEQ ID NO: 1 (e.g., one or more of SEQ ID NO: 2, SEQ ID NO: 3, SEQ ID NO: 4, and SEQ ID NO: 5). Examples of commercially available ACTH peptides that are compatible with the methods described herein include and are not limited to Adrenocorticotropic Hormone (ACTH) (1-24) (which is invariant across the mammalian genera), Adrenocorticotropic Hormone (ACTH) (1-39) (human), Adrenocorticotropic Hormone (ACTH) (1-39) (rat), or the like available from, for example, GenScript. $ACTH_{1-24}$ possesses biological activity equivalent to that of $ACTH_{1-39}$ and lesser activity of sequences comprising $ACTH_{1-19}$ through $ACTH_{1-23}$ is believed to be secondary, not to lessened receptor affinity but to an enhanced rate of in vivo degradation. Peptide sequences smaller than 1-18 exhibit markedly diminished activity at the MC2 receptor (Krieger 1982) in comparison to $ACTH_{1-24}$ and higher. The C-terminal 25-39 appears to influence the degradation of the molecule, so that human 1-39 has a longer duration of action than 1-24 (Baumann and Felber, 1976). Hofmann et al. (1970) also published results showing partial agonist activity of $ACTH_{1-23}$ and $5Gln-ACTH_{1-20}$ in adrenal stimulation assays: 91% and 80% respectively in comparison to $ACTH_{1-24}$ as control.

ACTH may also bind the other melanocortin receptors, ie, MC1r, MC3r, MC4r and MC5r, although it is a less potent agonist at these receptors than some of the smaller length melanocortin peptides.

The term "ACTH analog" or "analog of ACTH" refers to any compounds in which one or more atoms, functional groups, or substructures or amino acids, particularly conservative amino acid substitutions, in ACTH or fragments of ACTH have been replaced with different atoms, groups, or substructures or amino acids, or substitution of L-stereoisomers with D-stereoisomers of the amino acids while retaining the functional activity of the ACTH or fragments of ACTH. In some embodiments, an ACTH analog is a peptide segment of $ACTH_{1-39}$ peptide that retains biological activity of ACTH.

The term "ACTH complex" refers to ACTH or fragments or analogs thereof that are optionally complexed with other proteins (e.g., Bovine Serum Albumin) or metal ions, or fragments of ACTH, or any other suitable complexes that retain the functional characteristics of ACTH or ACTH fragments or analogs thereof and/or allow for formulation of ACTH or ACTH fragments or analogs thereof into suitable dosage forms.

The term "prodrug" refers to a precursor molecule that is a derivative of ACTH or ACTH fragments or analogs thereof that is suitable for incorporation in any dosage form described herein. A "prodrug" refers to a precursor compound that is converted into active compound in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, prodrugs facilitate transmittal across a cell membrane where water solubility is detrimental to mobility but which then is metabolically hydrolyzed to the carboxylic acid, the active entity, once inside the cell where water-solubility is beneficial. As non-limiting examples, a prodrug of ACTH or fragment of analog thereof is metabolically stable and is not degraded in the stomach.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or less labile and/or confers solubility or some other property to the drug. Once the chemical group has been cleaved and/or modified from the prodrug the active drug is generated. In some embodiments, a prodrug of ACTH or fragment or analog thereof is an alkyl ester of the parent compound such as, for example, methyl ester, ethyl ester, n-propyl ester, iso-propyl ester, n-butyl ester, sec-butyl ester, tert-butyl ester or any other ester.

"U", when appended to dosage amounts, designates a standardized unit of biologic activity as measured by the USP assay for repository corticotropin injection, which provides uniformity of dosing of a hormone peptide, and is expressed as the standardized units of activity per mL, such as, for example, 80 U/mL.

Methods

Provided herein are methods of preventing or treating ARDS comprising administration of adrenocorticotropic hormone (ACTH) peptide or fragment, analog, complex or aggregate thereof, or any combination thereof, as described herein, to individuals in need thereof. In some embodiments, methods of treatment of ARDS described herein allow for down-regulation of systemic inflammation and/or restoration of tissue homeostasis. In some embodiments, provided herein are methods of treatment of lung dysfunction in patients with $PaO_2/FiO_2$=100-199 comprising administration of adrenocorticotropic hormone (ACTH) peptide or fragment, analog, complex or aggregate thereof, or any combination thereof, as described herein, to individuals in need thereof. In some embodiments, provided herein are methods of treatment of lung dysfunction in patients with $PaO_2/FiO_2$<100 comprising administration of adrenocorticotropic hormone (ACTH) peptide or fragment, analog, complex or aggregate thereof, or any combination thereof, as described herein, to individuals in need thereof.

In some embodiments, provided herein is a method of treating an individual diagnosed with or suspected of having, or preventing in an individual at risk for developing, acute respiratory distress syndrome (ARDS) comprising administration of a therapeutically effective amount of an adrenocorticotropic hormone (ACTH) peptide, or fragment, analog, complex or aggregate thereof, or any combination thereof, to an individual in need thereof, provided that the adrenocorticotropic hormone (ACTH) peptide, or fragment, analog, complex or aggregate thereof, or any combination thereof, does not comprise α-MSH.

Dosing Regimen

In some embodiments, the ACTH peptide or fragment, analog, complex or aggregate thereof, or any combination thereof, may be administered as a first dose, followed by one or more subsequent doses. In some embodiments of the methods of treatment of ARDS described herein, the first dose and one or more subsequent doses of ACTH or fragment, analog, complex or aggregate thereof, or any combination thereof, are administered in a dosing regimen that is not continuous (e.g., the intervals between doses are uneven). In some embodiments of the methods of treatment of ARDS described above, the first dose and one or more subsequent doses of ACTH or fragment, analog, complex or aggregate thereof, or any combination thereof, are administered in a dosing regimen that is a continuous dosing regimen. In some embodiments, the ACTH peptide or fragment, analog, complex or aggregate thereof, or any combination thereof, may be administered as a first dose, followed by one or more subsequent doses, wherein the subsequent dose values are equivalent to the initial dose value. In some embodiments, the ACTH peptide or fragment, analog, complex or aggregate thereof, or any combination thereof, may be administered as a first dose, followed by one or more subsequent doses, wherein the subsequent dose values are not equivalent to the initial dose value. In some embodiments, the first dose is administered upon detection of one or more symptoms of ARDS in a clinically diagnosed ARDS patient. In some embodiments, the one or more subsequent doses are administered every day, every other day, every two days, every three days, every four days, every 5 days, every 6 days, once a week, every two weeks, every three weeks, once a month, every six weeks, every two months, every three months, every four months five months, every six months or any combination thereof. In some embodiments, the one or more subsequent doses are administered within the same day, and the dosing is continued as needed. In some embodiments, the ACTH peptide or fragment, analog, complex or aggregate thereof is administered at onset of ARDS and multiple times a day, every day, about every 2 days, about every 5 days, about every week, about every two weeks, about every three weeks, about every month, about every two months, or any combination thereof as needed. In some embodiments, the ACTH peptide or fragment, analog, complex or aggregate thereof is administered at one or more intervals during a day, about every day, about every 2 days, about every 5 days, about every week, about every two weeks, about every three weeks, about every month, about every two months, or any combination thereof before onset of ARDS and for as long as the patient experiences ARDS symptoms in the absence of said ACTH peptide or fragment, analog, complex or aggregate thereof.

In some embodiments, the dose comprises a first phase of dosing of about 4 to about 10 days duration wherein a patient receives a daily dose of 64 U daily or in a divided dose of 32 U administered at a selected interval within each day, followed by one or more subsequent phases of about 4 to about 10 days duration each wherein each successive phase of doses is about 50% of the dose of the preceding phase, and a final phase in which the dose of the preceding phase is administered at intervals of every other day.

In some embodiments, the dose comprises a first phase of dosing of about 7 days duration wherein the dose is administered as 64 U once per day or 32 U twice a day, followed by a second phase of about 7 days duration wherein the daily, or twice daily, dose is reduced by about 50%, followed by a third phase of about 7 days duration wherein the daily, or twice daily, dose of the second phase is reduced by about 50% and followed by a fourth phase of about 7 days, wherein the dose of the third phase is administered every other day.

In some embodiments the dose and frequency of dosing are as set out in Table I.

TABLE I

| Day | Dose and Frequency |
| --- | --- |
| 1-7 | Administer 64 U once daily |
| 8-14 | Decrease administration to 32 U once daily |
| 15-21 | Decrease administration to 16 U once daily |
| 22-28 | Administer 16 U every other day |

In some embodiments the dose and frequency of dosing are as set out in Table II.

TABLE II

| Day | Dose and Frequency |
| --- | --- |
| 1-7 | Administer 32U or 16 U in divided doses twice daily |
| 8-14 | Decrease administration to 16 U or 8 U in divided doses twice daily |
| 15-21 | Administer 16 U or 8 U once daily |
| 22-28 | Administer 16 U or 8 U once every other day. |

In some embodiments, the dosing regimen comprises doses that produce decreasing levels of drug early in the dosing interval followed by a prolonged dose-free interval. In some embodiments, the dosing regimen comprises a first dose, a series of subsequent doses, followed by a drug holiday, and then, one or more series of doses that are the same as or different from the first series of doses. By way of example only, in one dosing regimen, the methods of treatment of ARDS described above comprise administration of ACTH or fragment, analog, complex or aggregate thereof, or any combination thereof, and comprise a first dose of 80 U, then a once daily dose of 20 U for three days, followed by a 40 U dose every week for a month, followed by a period of no treatment for 3 months, and then a second series of doses comprising a first dose of 60 U, then a once daily dose of 20 U for three days, followed by a 40 U dose every week for a month, followed by a period of no treatment for 3 months.

In some embodiments, a dosing regimen comprises dosing that produces escalating levels of drug early in the dosing interval followed by a prolonged dose-free period. By way of example only, in one dosing regimen, the methods of treatment of ARDS describe above comprise administration of ACTH or fragment, analog, complex or aggregate thereof, or any combination thereof, and comprise a first dose of 20 U, a second dose of 20 U in the same week, then 40 U twice a week, then 40 U every other month for three months.

In some embodiments, a first dose of ACTH or fragment, analog, complex or aggregate thereof, or any combination thereof, is between about 10 U, 20 U, 30 U, 40 U, 50 U, 60 U, 70 U, 80 U and about 50 U, 60 U, 70 U, 80 U, 90 U, 100 U, 110 U, 120 U, 130 U, 140 U, 150 U or 200 U. In some embodiments, a first dose of ACTH or fragment, analog, complex or aggregate thereof, or any combination thereof, is between about 10 U to about 200 U, between about 10 U to about 150 U, between about 10 U to about 100 U, between about 10 U to about 80 U, between about 10 U to about 60 U, or between about 10 U to about 40 U. In some embodiments, a first dose of ACTH or fragment, analog, complex or aggregate thereof, or any combination thereof, is between about 10 U to about 200 U, between about 20 U to about 200 U, between about 40 U to about 200 U, between about 40 U to about 150 U, between about 40 U to about 100 U, between about 40 U to about 80 U, or between about 40 U to about 60 U. In some embodiments, a first dose of ACTH or fragment, analog, complex or aggregate thereof, or any combination thereof, is between about 20 U to about 200 U, between about 60 U to about 150 U, between about 60 U to about 100 U, or between about 60 U to about 80 U.

In some embodiments, one or more subsequent dose of ACTH or fragment, analog, complex or aggregate thereof, or any combination thereof, is between about 10 U, 20 U, 30 U, 40 U, 50 U, 60 U, 70 U, 80 U to about 50 U, 60 U, 70 U, 80 U, 90 U, 100 U, 110 U, 120 U, 130 U, 140 U, 150 U or 200 U. In some embodiments, a one or more subsequent dose of ACTH or fragment, analog, complex or aggregate thereof, or any combination thereof, is between about 10 U to about 200 U, between about 10 U to about 150 U, between about 10 U to about 100 U, between about 10 U to about 80 U, between about 10 U to about 60 U, or between about 10 U to about 40 U. In some embodiments, a one or more subsequent dose of ACTH or fragment, analog, complex or aggregate thereof, or any combination thereof, is between about 20 U to about 200 U, between about 20 U to about 150 U, between about 20 U to about 100 U, between about 20 U to about 80 U, or between about 20 U to about 60 U, or between about 20 U to about 40 U. In some embodiments, a one or more subsequent dose of ACTH or fragment, analog, complex or aggregate thereof, or any combination thereof, is between about 40 U to about 200 U, between about 40 U to about 150 U, between about 40 U to about 100 U, between about 40 U to about 80 U, or between about 40 U to about 60 U. In some embodiments, a one or more subsequent dose of ACTH or fragment, analog, complex or aggregate thereof, or any combination thereof, is between about 20 U to about 200 U, between about 60 U to about 150 U, between about 60 U to about 100 U, or between about 60 U to about 80 U.

In some embodiments, the ACTH, or fragment, analog, complex or aggregate thereof, or any combination thereof, is administered as a synthetic preparation (i.e., not naturally occurring), wherein a first dose of ACTH or fragment, analog, complex or aggregate thereof, or any combination thereof, is between about 10 mg/kg, 20 mg/kg, 30 mg/kg, 40 mg/kg, 50 mg/kg, 60 mg/kg, 70 mg/kg, 80 mg/kg to about 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or 200 mg/kg. In some embodiments, a first dose of ACTH or fragment, analog, complex or aggregate thereof, or any combination thereof, is between about 10 mg/kg to about 200 mg/kg, between about 20 mg/kg to about 200 mg/kg, between about 20 mg/kg to about 150 mg/kg, between about 20 mg/kg to about 100 mg/kg, between about 20 mg/kg to about 80 mg/kg, between about 20 mg/kg to about 60 mg/kg, or between about 20 mg/kg to about 40 mg/kg. In some embodiments, a first dose of ACTH or fragment, analog, complex or aggregate thereof, or any combination thereof, is between about 40 mg/kg to about 200 mg/kg, between about 40 mg/kg to about 150 mg/kg, between about 40 mg/kg to about 100 mg/kg, between about 40 mg/kg to about 80 mg/kg, or between about 40 mg/kg to about 60 mg/kg. In some embodiments, a first dose of ACTH or fragment, analog, complex or aggregate thereof, or any combination thereof, is between about 20 mg/kg to about 200 mg/kg, between about 60 mg/kg to about 150 mg/kg, between about 60 mg/kg to about 100 mg/kg, or between about 60 mg/kg to about 80 mg/kg.

Where the ACTH, or fragment, analog, complex or aggregate thereof, or any combination thereof, is a synthetic preparation (i.e., not naturally occurring), in some embodiments, one or more subsequent dose of ACTH or fragment, analog, complex or aggregate thereof, or any combination thereof, is between about 10 mg/kg, 20 mg/kg, 30 mg/kg, 40 mg/kg, 50 mg/kg, 60 mg/kg, 70 mg/kg, 80 mg/kg to about 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or 200 mg/kg. In some embodiments, one or more subsequent dose of ACTH or fragment, analog, complex or aggregate thereof, or any combination thereof, is between about 10 mg/kg to about 200 mg/kg, between about 10 mg/kg to about 150 mg/kg, between about 10 mg/kg to about 100 mg/kg, between about 10 mg/kg to about 80 mg/kg, between about 10 mg/kg to about 60 mg/kg, or between about 10 mg/kg to about 40 mg/kg. In some embodiments, one or more subsequent dose of ACTH or fragment, analog, complex or aggregate thereof, or any combination thereof, is between about 20 mg/kg to about 200 mg/kg, between about 20 mg/kg to about 150 mg/kg, between about 20 mg/kg to about 100 mg/kg, between about 20 mg/kg to about 80 mg/kg, or between about 20 mg/kg to about 60 mg/kg. In some embodiments, a one or more subsequent dose of ACTH or fragment, analog, complex or aggregate thereof, or any combination thereof, is between about 40 mg/kg to about 200 mg/kg, between about 40 mg/kg to about 150 mg/kg, between about 40 mg/kg to about 100 mg/kg, between about 40 mg/kg to about 80 mg/kg, or between about 40 mg/kg to about 60 mg/kg. In some embodiments a one or more subsequent dose of ACTH or fragment, analog, complex or aggregate thereof, or any combination thereof, is between about 20 mg/kg to about 200 mg/kg, between about 60 mg/kg to about 150 mg/kg, between about 60 mg/kg to about 100 mg/kg, or between about 60 mg/kg to about 80 mg/kg.

In some embodiments, a first dose of ACTH (e.g, synthetically produced $ACTH_{1-24}$) or fragment, analog, complex or aggregate thereof, or any combination thereof, is between about 0.01 mg to about 10 mg, between about 0.1 mg to about 2.5 mg, between about 0.5 mg to about 1 mg, or between about 2 mg to about 5 mg. In some embodiments, a first dose of ACTH or fragment, analog, complex or aggregate thereof, or any combination thereof is about 0.25 mg, about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg.

In some embodiments, one or more subsequent dose of ACTH (e.g, synthetically produced $ACTH_{1-24}$) or fragment, analog, complex or aggregate thereof, or any combination thereof, is between about 0.01 mg to about 10 mg, between about 0.1 mg to about 2.5 mg, between about 0.5 mg to about 1 mg, or between about 2 mg to about 5 mg. In some embodiments, one or more subsequent dose of ACTH or fragment, analog, complex or aggregate thereof, or any combination thereof is about 0.25 mg, about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg.

In some embodiments, one or more subsequent dose of ACTH or fragment, analog, complex or aggregate thereof, or any combination thereof, is between about 10% and about 90%, between about 20% and about 80%, between about 20% and about 60%, or between about 20%- and about 40% of the first dose of ACTH or fragment, analog, complex or aggregate thereof, or any combination thereof. In some embodiments, one or more subsequent dose of ACTH or fragment, analog, complex or aggregate thereof, or any combination thereof, is between about 80% and about 200%, between about 80% and about 175%, between about 80% and about 150%, between about 80% and about 125%, between about 80% and about 100%, between about 100% and 200%, between about 100% and 150%, or between about 100% and 120% of the first dose of ACTH or fragment, analog, complex or aggregate thereof, or any combination thereof. In some embodiments, one or more subsequent dose of ACTH or fragment, analog, complex or aggregate thereof, or any combination thereof, is 100% of the first dose of ACTH or fragment, analog, complex or aggregate thereof, or any combination thereof.

In some embodiments, the ACTH peptide or fragment, analog, complex or aggregate thereof, or any combination thereof, is administered to an individual in need thereof in an amount sufficient to provide plasma cortisol secretion levels between about 1.1 to about 10 times 1.1 to about 8 times, 1.1 to about 6 times, 1.1 to about 4 times, between about 1.1 to about 3 times, between about 1.1 to about 2 times, between about 1.1 to about 1.5 times the plasma cortisol secretion levels of a normal individual at about 8 am. In some embodiments, the ACTH peptide or fragment, analog, complex or aggregate thereof, or any combination thereof, is administered to an individual in need thereof in an amount sufficient to provide plasma cortisol secretion levels between about 1.5 to about 4 times, between about 1.5 to about 3 times, or between about 1.15 to about 2 times, the plasma cortisol secretion levels of a normal individual at about 8 am.

In some embodiments, the ACTH peptide or fragment, analog, complex or aggregate thereof, or any combination thereof, is administered to an individual in need thereof in an amount sufficient to provide plasma cortisol secretion levels between about 1.1 to about 10 times 1.1 to about 8 times, 1.1 to about 6 times, 1.1 to about 4 times, between about 1.1 to about 3 times, between about 1.1 to about 2 times, or between about 1.1 to about 1.5 times the plasma cortisol secretion levels prior to administration of the ACTH peptide or fragment, analog, complex or aggregate thereof, or any combination thereof. In some embodiments, the ACTH peptide or fragment, analog, complex or aggregate thereof, or any combination thereof, is administered to an individual in need thereof in an amount sufficient to provide plasma cortisol secretion levels between about 1.5 to about 4 times, between about 1.5 to about 3 times, or between about 1.15 to about 2 times, the plasma cortisol secretion levels prior to administration of the ACTH peptide or fragment, analog, complex or aggregate thereof, or any combination thereof.

In some embodiments, the ACTH peptide or fragment, analog, complex or aggregate thereof, or any combination thereof, is administered in an amount sufficient to provide plasma cortisol concentration between about 1.5 to about 120 µg/100 mL over at least 24 hours after administration. In some embodiments, the ACTH peptide or fragment, analog, complex or aggregate thereof, or any combination thereof, is administered in an amount sufficient to provide plasma cortisol concentration between about 1.5 to about 60 µg/100 mL over at least 24 hours after administration. In some embodiments, the ACTH peptide or fragment, analog, complex or aggregate thereof, or any combination thereof, is administered in an amount sufficient to provide plasma cortisol concentration between about 1.5 to about 30 µg/100 mL over at least 24 hours after administration.

In some embodiments, where the patient's condition does not improve upon administration of a dosing regimen described herein, upon the doctor's discretion the ACTH peptide or fragment, analog, complex or aggregate thereof, or any combination thereof is optionally administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the ACTH peptide or fragment, analog, complex or aggregate thereof, or any combination thereof is optionally given continuously; alternatively, the dose of ACTH peptide or fragment, analog, complex or aggregate thereof, or any combination thereof being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, the pharmaceutical compositions described herein are in unit dosage forms suitable for single administration of precise dosages. In unit dosage form, the formulation is divided into unit doses containing appropriate quantities of ACTH peptide or fragment, analog, complex or aggregate thereof, or any combination thereof. In some embodiments, the unit dosage is in the form of a package containing discrete quantities of the formulation. Non-limiting examples are packaged tablets or capsules, powders in vials or ampoules, or injectable suspension or solution in ampoules. In some embodiments, aqueous suspension compositions are packaged in single-dose non-reclosable containers. Alternatively, multiple-dose reclosable containers are used. In some of such embodiments, a preservative is optionally included in the composition. By way of example only, formulations for intramuscular injection are presented in unit dosage form, which include, but are not limited to ampoules, or in multi dose containers with a rubber septum or similar structure suitable for withdrawing a dose via syringe and with an added preservative.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. ACTH peptide or fragment, analog, complex or aggregate thereof, or any combination thereof, exhibiting high therapeutic indices are preferred. The data obtained from cell culture assays and animal studies is optionally used in formulating a range of dosage for use in human. The dosage of such ACTH peptide or fragment, analog, complex or aggregate thereof, or any combination thereof lies preferably within a range of circulating concentrations that include the ED50 with minimal toxicity. The dosage optionally varies within this range depending upon the dosage form employed and the route of administration utilized.

Combination Therapy

In some embodiments of the methods and dosing regimens described above, ACTH peptide or fragment, analog, complex or aggregate thereof, or any combination thereof, is administered in combination with other treatments including, and not limited to, ventilation, mechanical ventilation (including newer modes of mechanical ventilation including, but not limited to, high frequency oscillatory ventilation), a glucocorticoid, a surfactant, inhaled nitric oxide, an antioxidant, a protease inhibitor, a recombinant human activated protein C, a β2-agonist, lisofylline, a statin, inhaled heparin, a diuretic, a sedative, an analgesic, a muscle relaxant, an antibiotic, inhaled prostacyclin, inhaled synthetic prostacyclin analog, ketoconazole, alprostadil, keratinocyte growth factor, beta-agonists, human mAb against TS factor 7a, interferon receptor agonists, insulin, perfluorocarbon, budesonide, recombinant human ACE, recombinant human CC10 protein, tissue plasminogen activator, human mesenchymal stem cells, or nutritional therapy. In other embodiments of combination therapy, the other treatment included is a glucocorticoid, such as, for example, methylprednisolone, dexamethasone, prednisone, prednisolone, betamethasone, triamcinolone, triamcinolone acetonide budesonide, and beclometasone; beta-agonists, such as, for example, albuterol; lisofylline; rosuvastatin, inhaled heparin; inhaled nitric oxide; recombinant human activated protein C; NSAIDS, such as, for example, ibuprofen; naproxen, and acetaminophen; cisatracurium besylate; procysteine; acetylcysteine; inhaled prostacyclin; ketoconazole; alprostadil; keratinocyte growth factor; human mAb against TS factor 7a; insulin; perfluorocarbons, recombinant human ACE; recombinant human CC10 protein; tissue plasminogen activator; human mesenchymal stem cells; or nutritional therapy such as a combination of omega-3 fatty acids, antioxidants, and γ-linolenic acids with isocaloric foods and extracorporeal membrane oxygenation (ECMO).

NSAIDS include, but are not limited to, aspirin, acetaminophen, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, and firocoxib.

Analgesics include, but are not limited to, NSAIDS and opioids (narcotics). Opioids include, but are not limited to, dextropropoxyphene, codeine, tramadol, tapentadol, anileridine, alphaprodine, pethidine, hydocodone, morphine, oxycodone, methadone, diamorphine, hydromorphone, oxymorphone, levorphanol, 7-hydroxymitragynine, buprenorphine, fentanyl, sufentanil, bromadol, etorphine, dihydroetorphine, and carfentanil.

Glucocorticoids include, but are not limited to, hydrocortisone, cortisone, prednisone, prednisolone, methylprednisolone, dexamethasone, betamethasone, triamcinolone, beclometasone, or fludrocortisones.

In some embodiments of combination therapy, the ACTH peptide or fragment, analog, complex or aggregate thereof, or any combination thereof, and the second therapeutic treatment are administered simultaneously. In some embodiments of combination therapy, the ACTH peptide or fragment, analog, complex or aggregate thereof, or any combination thereof, and the second therapeutic treatment are administered serially in any order. In some embodiments of combination therapy, the ACTH peptide or fragment, analog, complex or aggregate thereof, or any combination thereof, and the second therapeutic treatment are administered at different intervals. By way of example only, a second therapeutic treatment is administered after completion of a dosing regimen comprising administration of ACTH peptide or fragment, analog, complex or aggregate thereof, or any combination thereof.

Pharmaceutical Formulations

Provided herein, in certain embodiments, are compositions comprising at least one ACTH peptide or fragment, analog, complex or aggregate thereof, or any combination thereof, where the ACTH peptide or fragment, analog, complex or aggregate thereof, or any combination thereof, is as described herein.

Pharmaceutical compositions are formulated using one or more physiologically acceptable carriers including excipients and auxiliaries which facilitate processing of the ACTH peptide or fragment, analog, complex or aggregate thereof, or any combination thereof, into preparations which are used pharmaceutically. Proper formulation is dependent upon the route of administration chosen. A summary of pharmaceutical compositions is found, for example, in Remington: The Science and Practice of Pharmacy, Nineteenth Ed (Ea hston, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include one or more of ACTH peptide or fragment, analog, complex or aggregate thereof, or any combination thereof, and a pharmaceutically acceptable diluent(s), excipient(s), or carrier(s). In addition, the ACTH peptide or fragment, analog, complex or aggregate thereof, or any combination thereof, is optionally administered as pharmaceutical compositions in which it is mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition, as used herein, refers to a mixture of ACTH peptide or fragment, analog, complex or aggregate thereof, or any combination thereof, with other chemical components, such as carriers, stabilizers, diluents, dispersing agents, suspending agents, thickening agents, and/or excipients. In some embodiments, a pharmaceutical composition comprises an ACTH preparation (e.g., an ACTH peptide or fragment, analog, complex or aggregate thereof, or any combination thereof, and any other proteins and/or other substances that are present in a homogenized pituitary extract obtained from an appropriate animal source) and other chemical components, such as carriers, stabilizers, diluents, dispersing agents, suspending agents, thickening agents, and/or excipients. The pharmaceutical composition facilitates administration of ACTH peptide or fragment, analog, complex or aggregate thereof, or any combination thereof, to an organism. In practicing the methods of treatment or use provided herein, an ACTH peptide or fragment, analog, complex or aggregate thereof, or any combination thereof, are administered in a pharmaceutical composition to a mammal having a condition, disease, or disorder to be treated. Preferably, the mammal is a human. The does and dosing regimen varies depending on the severity and stage of the condition, the age and relative health of an individual, the potency of ACTH peptide or fragment, analog, complex or aggregate thereof, or any combination thereof, used and other factors. The ACTH peptide or fragment, analog, complex or aggregate thereof, or any combination thereof, is optionally used singly or in combination with one or more therapeutic agents as components of mixtures.

The pharmaceutical formulations described herein are optionally administered to a individual by multiple administration routes, including but not limited to, oral, parenteral (e.g., intravenous, subcutaneous, intramuscular, intrathecal), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical compositions will include at least one ACTH peptide or fragment, analog, complex or aggregate thereof, or any combination thereof, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of ACTH peptide or fragment, analog, complex or aggregate thereof, or any combination thereof, having the same type of activity. In some situations, ACTH peptide or fragment, analog, complex or aggregate thereof, or any combination thereof, exist as tautomers and/or rotational isomers. All tautomers and/or rotational isomers are included within the scope of the embodiments presented herein. Additionally, ACTH peptide or fragment, analog, complex or aggregate thereof, or any combination thereof, exists in unsolvated as well as solvated forms with pharmaceutically acceptable solvents such as water, ethanol, and the like. The solvated forms of the ACTH peptide or fragment, analog, complex or aggregate thereof, or any combination thereof, presented herein are also considered to be disclosed herein. In some embodiments, ACTH peptide or fragment, analog, complex or aggregate thereof, or any combination thereof, exists as a complex with metal ions, including, for example, $Zn^{+2}$ ions. The metal-ion complexed forms of the ACTH peptide or fragment, analog, complex or aggregate thereof, or any combination thereof, presented herein are also considered to be disclosed herein.

"Carrier materials" include any commonly used excipients in pharmaceutics and should be selected on the basis of compatibility with ACTH peptide or fragment, analog, complex or aggregate thereof, or any combination thereof, disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

Moreover, the pharmaceutical compositions described herein, which include a ACTH peptide or fragment, analog, complex or aggregate thereof, or any combination thereof, are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, a formulation comprising a ACTH peptide or fragment, analog, complex or aggregate thereof, or any combination thereof, is a solid drug dispersion. A solid dispersion is a dispersion of one or more active ingredients in an inert carrier or matrix at solid state prepared by the melting (or fusion), solvent, or melting-solvent methods. (Chiou and Riegelman, Journal of Pharmaceutical Sciences, 60, 1281 (1971)). The dispersion of one or more active agents in a solid diluent is achieved without mechanical mixing. Solid dispersions are also called solid-state dispersions. In some embodiments, any ACTH peptide or fragment, analog, complex or aggregate thereof, or any combination thereof, described is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion. In some embodiments, such amorphous dispersions are filled in capsules and/or constituted into powders for reconstitution. Solubility of an SDD comprising a drug is higher than the solubility of a crystalline form of a drug or a non-SDD amorphous form of a drug. In some embodiments of the methods described herein, ACTH peptide or fragment, analog, complex or aggregate thereof, or any combination thereof, are administered as SDDs constituted into appropriate dosage forms described herein.

Pharmaceutical preparations for oral use are optionally obtained by mixing one or more solid excipient with a ACTH peptide or fragment, analog, complex or aggregate thereof, or any combination thereof, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate. In some embodiments, a prodrug of the ACTH peptide or fragment, analog, complex or aggregate thereof, or any combination thereof, is used in preprations for oral use.

Dragee cores are provided with suitable coatings. For this purpose, concentrated sugar solutions are generally used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are optionally added to the tablets or dragee coatings for identification or to characterize different combinations of active compound doses.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of a ACTH peptide or fragment, analog, complex or aggregate thereof, or any combination thereof, are optionally administered as a single capsule or in multiple capsule dosage form. In some embodiments, the pharmaceutical formulation is administered in two, or three, or four, capsules or tablets.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including a ACTH peptide or fragment, analog, complex or aggregate thereof, or any combination thereof, include, but are not limited to, hydroxypropyl cellulose ethers (HPC) such as KLUCEL® (hydroxypropylcellulose) or Nisso HPC, low-substituted hydroxypropyl cellulose ethers (L-HPC), hydroxypropyl methyl cellulose ethers (HPMC) such as Seppifilm-LC, PHARMACOAT® (hypromellose), METOLOSE SR (hypromellose), METHOCEL®-E (cellulose ethers), OPADRY® YS (one step film coating system), PrimaFlo, Benecel MP824, and Benecel MP843, methylcellulose polymers such as METHOCEL®-A (cellulose ethers), hydroxypropylmethylcellulose acetate stearate AQOAT® (HF-LS, HF-LG,HF-MS) and METOLOSE® (methylcellulose; hypromellose), Ethylcelluloses (EC) and mixtures thereof such as E461, ETHOCEL® (ethylcellulose polymers), AQUALON® EC (ethylcellulose), SURELEASE® (ethylcellulose dispersion), Polyvinyl alcohol (PVA) such as OPADRY® AMB (aqueous moisture barrier film coating system), hydroxyethylcelluloses such as NATROSOL®, carboxymethylcelluloses and salts of carboxymethylcelluloses (CMC) such as AQUALON®-CMC, polyvinyl alcohol and polyethylene glycol co-polymers such as KOLLICOAT IR® (ethylene glycol and vinyl alcohol graft copolymer), monoglycerides (Myverol®), triglycerides (KLX®), polyethylene glycols, modified food starch, acrylic polymers and mixtures of acrylic polymers with cellulose ethers such as EUDRAGIT® EPO (dimethylaminoethyl methacrylate copolymer), EUDRAGIT® L30D-55, EUDRAGIT® FS 30D, EUDRAGIT® L100-55, EUDRAGIT® L100, EUDRAGIT® S100, EUDRAGIT® RD100, EUDRAGIT® E100, EUDRAGIT® L12.5, EUDRAGIT® S12.5, EUDRAGIT® NE30D, and EUDRAGIT® NE 40D, cellulose acetate phthalate, sepifilms such as mixtures of HPMC and stearic acid, cyclodextrins, and mixtures of these materials.

The pharmaceutical solid oral dosage forms including formulations described herein, which include a ACTH peptide or fragment, analog, complex or aggregate thereof, or any combination thereof, are optionally further formulated to provide a controlled release of the ACTH peptide or fragment, analog, complex or aggregate thereof, or any combination thereof. Controlled release refers to the release of the ACTH peptide or fragment, analog, complex or aggregate thereof, or any combination thereof, from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a individual over an extended period of time according to a predetermined profile. Such release rates provide levels of ACTH peptide or fragment, analog, complex or aggregate thereof, or any combination thereof, for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations. In some embodiments, the formulations described herein, which include a ACTH peptide or fragment, analog, complex or aggregate thereof, or any combination thereof, are delivered using an implant. In some embodiments, the implants are formulated to provide a controlled release of the ACTH peptide or fragment, analog, complex or aggregate thereof, or any combination thereof. In some embodiments, the implant is an erodible implant.

In other embodiments, the formulations described herein, which include a ACTH peptide or fragment, analog, complex or aggregate thereof, or any combination thereof, are delivered using a pulsatile dosage form. A pulsatile dosage form is capable of providing one or more immediate release pulses at predetermined time points after a controlled lag time or at specific sites. Pulsatile dosage forms including the formulations described herein, which include a ACTH peptide or fragment, analog, complex or aggregate thereof, or any combination thereof, are optionally administered using a variety of pulsatile formulations that include, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the ACTH peptide or fragment, analog, complex or aggregate thereof, or any combination thereof, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Suitable intranasal formulations include those described in, for example, U.S. Pat. Nos. 4,476,116, 5,116,817 and 6,391,452. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present.

For administration by inhalation, the ACTH peptide or fragment, analog, complex or aggregate thereof, or any combination thereof, is optionally in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges of, such as, by way of example only, gelatin for use in an inhaler or insufflator are formulated containing a powder mix of the ACTH peptide or fragment, analog, complex or aggregate thereof, or any combination thereof, and a suitable powder base such as lactose or starch.

Buccal formulations that include an ACTH peptide or fragment, analog, complex or aggregate thereof, or any combination thereof, include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. The buccal dosage form is fabricated so as to erode gradually over a predetermined time period, wherein the delivery of the ACTH peptide or fragment, analog, complex or aggregate thereof, or any combination thereof, is provided essentially throughout. Buccal drug delivery avoids the disadvantages encountered with oral drug administration, e.g., slow absorption, degradation of the active agent by fluids present in the gastrointestinal tract and/or first-pass inactivation in the liver. The bioerodible (hydrolysable) polymeric carrier generally comprises hydrophilic (water-soluble and water-swellable) polymers that adhere to the wet surface of the buccal mucosa. Examples of polymeric carriers useful herein include acrylic acid polymers and co, e.g., those known as "carbomers" CARBOPOL®, which may be obtained from B.F. Goodrich, is one such polymer). Other components also be incorporated into the buccal dosage forms described herein include, but are not limited to, disintegrants, diluents, binders, lubricants, flavoring, colorants, preservatives, and the like. For buccal or sublingual administration, the compositions optionally take the form of tablets, lozenges, or gels formulated in a conventional manner.

Transdermal formulations of a ACTH peptide or fragment, analog, complex or aggregate thereof, or any combination thereof, are administered for example by those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal formulations described herein include at least three components: (1) a formulation of a ACTH peptide or fragment, analog, complex or aggregate thereof, or any combination thereof; (2) a penetration enhancer; and (3) an aqueous adjuvant. In addition, transdermal formulations include components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintain a saturated or supersaturated state to promote diffusion into the skin.

In some embodiments, formulations suitable for transdermal administration of a ACTH peptide or fragment, analog, complex or aggregate thereof, or any combination thereof, employ transdermal delivery devices and transdermal delivery patches and are lipophilic emulsions or buffered, aqueous solutions, dissolved and/or dispersed in a polymer or an adhesive. Such patches are optionally constructed for continuous, pulsatile, or on demand delivery of pharmaceutical agents. Still further, transdermal delivery of the ACTH peptide or fragment, analog, complex or aggregate thereof, or any combination thereof, is optionally accomplished by means of iontophoretic patches and the like. Additionally, transdermal patches provide controlled delivery of the ACTH peptide or fragment, analog, complex or aggregate thereof, or any combination thereof. The rate of absorption is optionally slowed by using rate-controlling membranes or by trapping the ACTH peptide or fragment, analog, complex or aggregate thereof, or any combination thereof, within a polymer matrix or gel. Conversely, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing the ACTH peptide or fragment, analog, complex or aggregate thereof, or any combination thereof, optionally with carriers, optionally a rate controlling barrier to deliver the ACTH peptide or fragment, analog, complex or aggregate thereof, or any combination thereof, to the skin of the host at a controlled and predetermined rate over a prolonged period of time, and means to secure the device to the skin.

Formulations that include a ACTH peptide or fragment, analog, complex or aggregate thereof, or any combination thereof, suitable for intramuscular, intrathecal, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, a ACTH peptide or fragment, analog, complex or aggregate thereof, or any combination thereof, is optionally formulated in aqueous solutions, preferably in physiologically compatible buffers such as Hank's solution, Ringer's solution, or physiological saline buffer. Alternatively, a ACTH peptide or fragment, analog, complex or aggregate thereof, or any combination thereof, is optionally formulated as a sterile powder for reconstitution into sterile solutions or dispersions for intravenous delivery. These ready-made or reconstituted solutions or dispersions for intravenous delivery can be packaged in sterile bags for intravenous drip. For transmucosal administration, penetrants appropriate to the barrier to be permeated are used in the formulation. For other parenteral injections including intrathecal and intramuscular injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of the ACTH peptide or fragment, analog, complex or aggregate thereof, or any combination thereof, in water soluble form, optionally including a gelling agent. Additionally, an ACTH peptide or fragment, analog, complex or aggregate thereof, or any combination thereof, may be prepared as a lyophilized powder for reconstitution with a physiologically suitable diluent.

In some embodiments, the ACTH peptide or fragment, analog, complex or aggregate thereof, or any combination thereof, is administered topically and formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

The ACTH peptide or fragment, analog, complex or aggregate thereof, or any combination thereof, is also optionally formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

EXAMPLES

Example 1: Bleomycin-Induced Lung Injury Animal Model

Male Wistar rats weighing 200-250 g are anesthetized by i.p. injection of 125 mg/kg ketamine. Tracheotomy is performed on all animals which are then subdivided into three groups (n=10) to receive i.t. saline (sham, group A); i.t. bleomycin and control treatment (group B); or i.t. bleomycin and active treatment (group C). The neck wound is closed, and the animals are returned to their cages and allowed free access to food and water.

Two hundred microliters of sterile saline (group A, sham) or 1 mg of bleomycin sulfate in 200 µL of sterile saline (groups B and C) are instilled into the lungs using a 25-gauge needle inserted between the cartilaginous rings of the trachea. Ten of the bleomycin-instilled animals receive an i.p. injection of 0.5 mL saline (group B). Ten of the bleomycin recipients are assigned to active treatment (group C) and receive i.p. injections of ACTH in 0.5 mL saline. Saline or ACTH are injected immediately before bleomycin instillation.

Five rats from each group (n=15) are anesthetized by ketamine at 8 h. A xiphopubic incision is done to expose the inferior vena cava and the lungs. Blood is collected from the inferior vena cava in heparinized syringes. The other animals are killed using the same procedure at 24 h; these rats receive a second i.p. injection of ACTH or saline at 12 h. Longitudinal sections of lung tissue are obtained from the right lung and a) are snap frozen in liquid nitrogen for RNA extraction, b) or are fixed in formalin and paraffin embedded for histology and immunohistochemistry. Left lungs are used to determine wet/dry (W/D) weight ratio.

Circulating NO is measured as an index of systemic inflammation. Lung edema is evaluated through histological examination and calculation of the W/D weight ratio. The frozen lung samples are used to obtain a gene expression profile to evaluate stress and inflammatory response.

Example 2: Endotoxin-Induced Lung Injury Animal Model

Three groups of rats (n=10 each) receive: intratracheal infusion of endotoxin (S. typhosa, 500 mg in 0.25 mL saline solution) plus i.p. injections of ACTH (in 0.2 mL solution) at 0, 2, and 4 hours postendotoxin treatment; intratracheal endoxin infusion plus saline injections; control intratracheal saline infusion plus saline injections.

Six hours after endotoxin administration the trachea is cannulated and the cannula is secured with silk thread. Cell medium (12 mL) is used to wash the pulmonary tree (injected and withdrawn five times); both the bronchoalveolar lavage (BAL) fluid and whole blood from the jugular vein are transferred to test tubes for analysis in a cell counter.

Therapeutic effect of ACTH on white blood cell (WBC) migration is assessed through comparison of WBC counts in BAL fluid and the blood.

Example 3: Clinical Trial of ACTHAR® (Adrenocorticotropic Hormone) in the Treatment of Acute Respiratory Distress Syndrome Purpose:

A randomized, double-blind, parallel group, placebo-controlled pilot safety and efficacy study compares three dosing regimens of ACTH to Placebo in patients with moderate or severe ARDS ($PaO_2/FiO_2 \leq 200$ mmHg with $PEEP \geq 5$ cm $H_2O$). A total of 130 patients are randomized.

Screening:

Patients are eligible for study enrollment if all screening criteria for ARDS are met within the same 24 hour window, and ARDS criteria persist for a minimum of 24 hours and a maximum of 10 days after the initial ARDS diagnosis is made and all inclusion/exclusion criteria are met. Total study duration for each patient including follow-up is approximately 60 days.

Study Procedure:

Treatment Period (28 days): At study Day 0, eligible patients undergo baseline assessments, randomization to treatment group, and the first dose of study medication is administered. Safety, tolerability and efficacy of study medication is assessed as long as the patient remains hospitalized. If a patient is discharged from the hospital prior to Day 28, a home visit occurs on Day 28 (±2 days) to conduct required assessments.

Follow-up Period (32 days): The Follow-Up Period begins immediately after the Treatment Period. Patients do not receive study medication during the Follow-Up Period. Day 60 is the last day of study participation for patients, and safety and efficacy assessments are performed.

Study Outcome Measures:

The primary outcome measure is the number of ventilator-free days (patient alive and breathing without assistance for ≥48 hours) by Day 28 after randomization.

The secondary outcome measures include time to successful liberation from ventilator support, defined as ≥48 hours alive and breathing without assistance (supplemental oxygen support is acceptable); number of organ failure-free days during the first 28 and 60 days; number of ICU-free and hospital free days during the first 28 and 60 days for all patients who survive to ICU and hospital discharge, respectively; change over time in PaO2/FiO2 ratio from baseline (Day 0) during the first 28 days; change over time in Lung Injury Score (LIS) from baseline (Day 0) during the first 28 days; change over time in Systemic Organ Failure Assessment Score (SOFA) score during the first 28 days; and mortality at Day 28 and Day 60.

Safety Endpoints:

Safety and tolerability are assessed by treatment-emergent adverse events; physical examinations; laboratory measurements including glycemic status, total daily dose of insulin (TDDI), serum cortisol, hematology, chemistry, and urinalysis; 12-lead electrocardiograms (ECGs); blood pressure (supine) measurement; and heart rate measurement.

Example 4: Pharmaceutical Compositions

Example 2a: Parenteral Composition

To prepare a parenteral pharmaceutical composition suitable for administration by intramuscular or subcutaneous injection, a water-soluble ACTH peptide or fragment, analog, complex or aggregate or salt thereof, or any combination thereof, for example, a highly purified sterile preparation of an analog of porcine adrenocorticotropic hormone is admixed with 16% gelatin and then dissolved in sterile, non-pyrogenic water for injection with addition of 0.5% phenol, not more than 0.1% cysteine (added), and sodium hydroxide and/or acetic acid as needed to adjust pH. The resulting gel mixture is incorporated into a multi dosage 5 mL vial of a form suitable for administration by injection, the potency of the composition is measured in USP units (designated as "U" which provides a standardized measure of activity) and a multi-dose vial may provide, for example 80 U/mL Example 2b: Inhalation Composition To prepare a pharmaceutical composition for inhalation delivery, 20 mg of ACTH peptide or fragment, analog, complex or aggregate thereof, or any combination thereof, is mixed with 50 mg of anhydrous citric acid and 100 mL of 0.9% sodium chloride solution. The mixture is incorporated into an inhalation delivery unit, such as a nebulizer, which is suitable for inhalation administration.

Example 2c: Rectal Gel Composition

To prepare a pharmaceutical composition for rectal delivery, 100 mg of ACTH peptide or fragment, analog, complex or aggregate thereof, or any combination thereof, is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 2d: Topical Gel Composition

To prepare a pharmaceutical topical gel composition, 100 mg of ACTH peptide or fragment, analog, complex or aggregate thereof, or any combination thereof, is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topicl administration.

Example 2e: Oral Composition

To prepare a pharmaceutical composition for oral delivery, 100 mg of ACTH peptide or fragment, analog, complex or aggregate thereof, or any combination thereof, or a prodrug thereof, is mixed with 750 mg of starch. The mixture is incorporated into an oral dosage unit, such as a hard gelatin capsule, which is suitable for oral administration.

Example 2f: Nasal Spray Solution

To prepare a pharmaceutical nasal spray solution, 10 g of ACTH peptide or fragment, analog, complex or aggregate thereof, or any combination thereof, is mixed with 30 mL of a 0.05M phosphate buffer solution (pH 4.4). The solution is placed in a nasal administrator designed to deliver 100 µl of spray for each application.

Example 5: Neutrophil Chemotaxis Assay

The objective of this study was to evaluate the effects of porcine $ACTH_{1-39}$ ($pACTH_{1-39}$) on in vitro chemotaxis of human neutrophils isolated from the blood of healthy human subjects (n=6) in response to IL-8, a potent neutrophil chemoattractant. Neutrophils play a role in the pathogenesis of ARDS, and the influx of neutrophils is often observed of patients with ARDS. IL-8 (interleukin-8) is a chemotactic factor implicated in the neutrophil recruitment in the lungs of ARDS patients (Clinical Science, 2008, 114, 403-412).

In this study, neutrophil chemotaxis was evaluated using a Boyden chamber assay. Four concentrations of $pACTH_{1-39}$ (0.1, 1, 10, 100 µg/mL) were tested in quadruplicate with cells isolated from each neutrophil donor (FIG. 1). Additional studies were performed that confirmed $pACTH_{1-39}$ did not exhibit cytotoxicity for human neutrophils. Data were analyzed using GraphPad Prism software and nonparametric analysis (Kruskal Wallis with Dunns multiple comparison post hoc tests). The results demonstrated that $pACTH_{1-39}$ attenuated IL-8 induced neutrophil chemotaxis in vitro.

Example 6: In Vivo Evaluation of Granulocyte Chemotaxis

Granulocyte chemotaxis in vivo was assessed by evaluating the effects of ACTHAR® (adrenocorticotropic hormone) on zymosan-induced peritonitis. In this model, heat-killed yeast particles (zymosan) are injected into the peritoneal cavity of mice. Zymosan activates complement, mast cells and peritoneal macrophages, generates proinflammatory mediators, and induces the migration of leukocytes into the peritoneal cavity. The infiltrating cells are primarily neutrophils, although monocytes also migrate at later time points.

Figure 2:
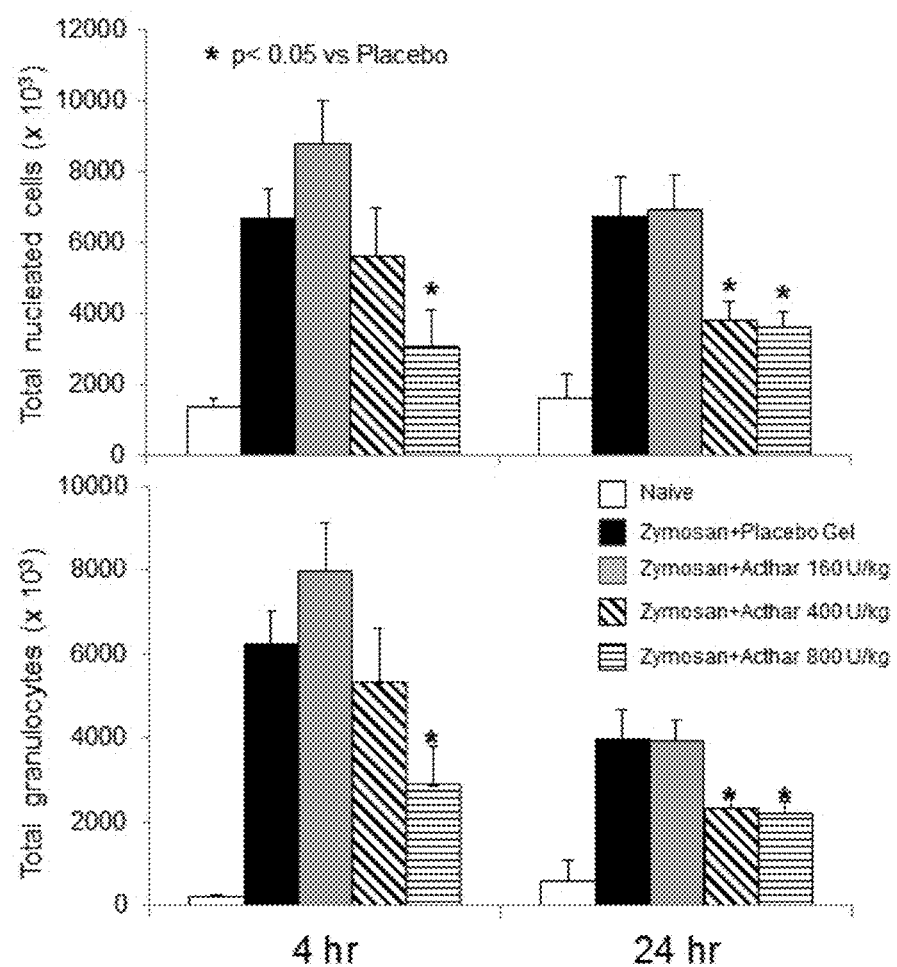
FIG. 2, described in Example 6, illustrates the results of granulocyte chemotaxis in vivo by evaluating the effects of ACTHAR® (adrenocorticotropic hormone) on zymosan-induced peritonitis.

ACTHAR® (adrenocorticotropic hormone) (160, 400 or 800 U/kg; n=8/group) or placebo gel (10 mL/kg; n=8/group) was administered to animals 1 hour before zymosan challenge. Separate groups of mice were sacrificed 4 hours and 24 hours post zymosan challenge, and lavage was performed to measure the number and type of leukocytes which migrated into the peritoneal cavity in response to zymosan. Results (FIG. 2) were compared to naïve animals not receiving zymosan (n=8/group). Additional groups of mice (not shown) received dexamethasone (1 mg/kg) or the same volume of vehicle control one hour prior to zymosan injection, as corticosteroid therapy serves as a positive control for efficacy in this model. Data were analyzed using GraphPad Prism software and nonparametric analysis (Kruskal Wallis with Dunns multiple comparison post hoc tests). This study demonstrated that ACTHAR® (adrenocorticotropic hormone) attenuated granulocyte chemotaxis in vivo.

Example 7: Detection of Total Antibodies (IgG) in B Cells

Figure 3:
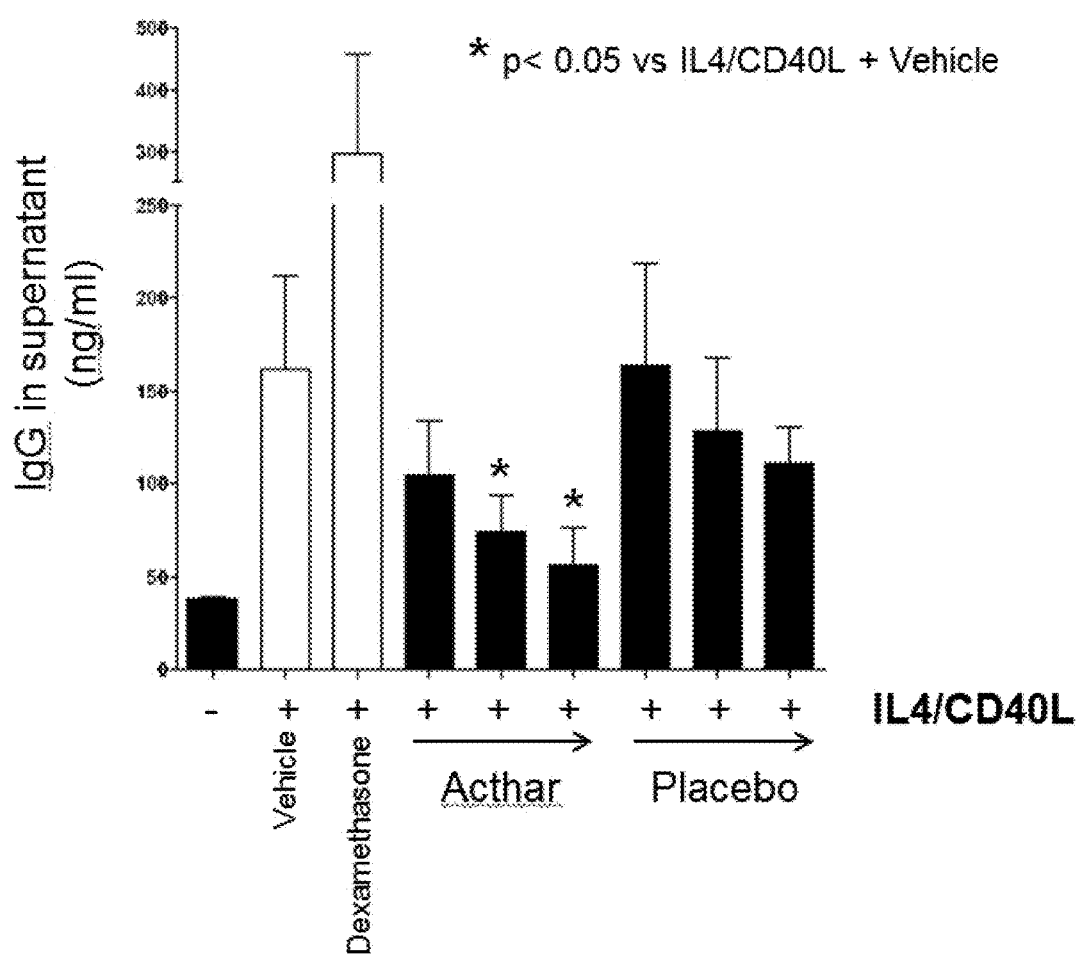
FIG. 3, described in Example 7, illustrates the effects of ACTHAR® (adrenocorticotropic hormone) on IgG production after B cell stimulation with IL4/CD40L.

This study was performed to evaluate the effects of ACTHAR® (adrenocorticotropic hormone) and placebo gel on IgG production from B cells isolated from healthy normal human subjects (n=5) and to assess effects of ACTHAR® (adrenocorticotropic hormone) on B cell proliferation and viability in response to stimulation with IL4/CD40L. Isolated B cells were cultured for 7 days in replicate cultures with proprietary dilutions of Acthar® or placebo gel, or with dexamethasone, with and without added CD40L/IL-4. Secreted total antibodies (IgG) in culture supernatants were measured using commercial ELISA kits. Data were analyzed using GraphPad Prism software and nonparametric analysis (Kruskal Wallis with Dunns multiple comparison post hoc tests). This results showed that ACTHAR® (adrenocorticotropic hormone) decreased in vitro antibody production after B cell stimulation with IL4/CD40L (FIG. 3).

Example 8: In Vivo Analysis of Antibody Production

Figure 4:
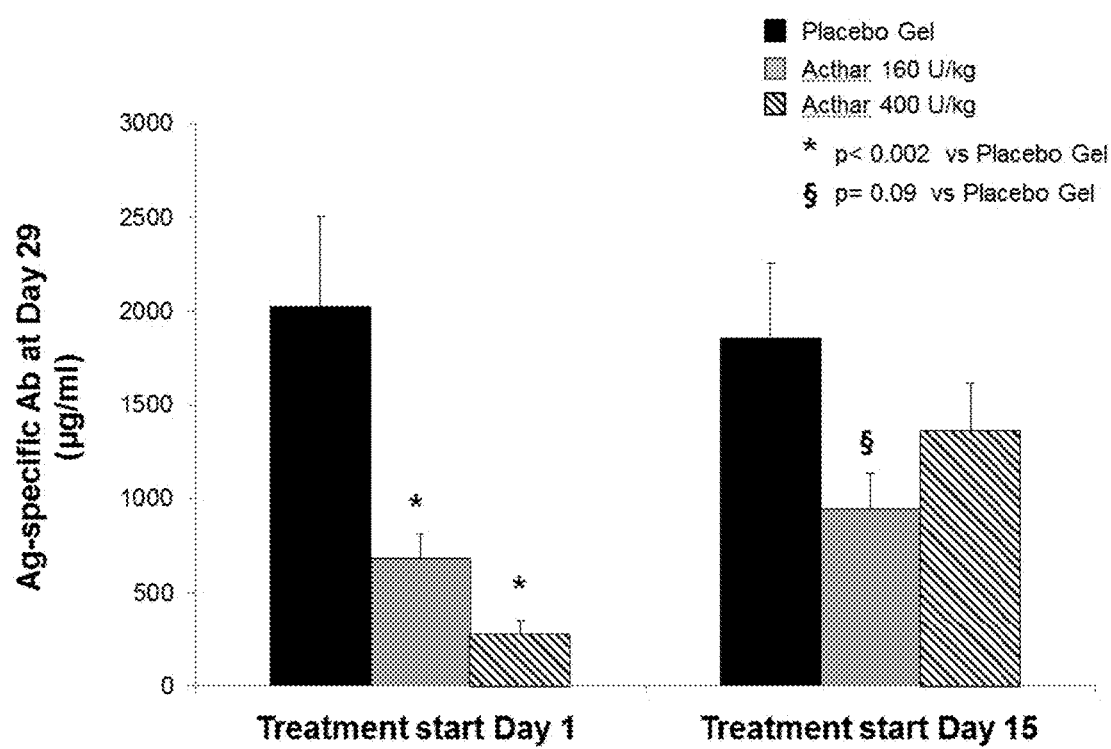
FIG. 4, described in Example 8, illustrates the effect of ACTHAR® (adrenocorticotropic hormone) on antibody production associated with antigen-specific immune response.

The objective of this study was to evaluate the effects of ACTHAR® (adrenocorticotropic hormone) and placebo gel on antibody production associated with both new and established antigen-specific immune responses. Mice were immunized with chicken ovalbumin (Ova) on Day 1 and again on Day 15. Treatment with ACTHAR® (adrenocorticotropic hormone) (160 or 400 U/kg) or placebo gel (5 mL/kg) was initiated either on Day 1, prior to immunization, or on Day 15 prior to immunization boost. Circulating serum anti Ova IgG1 levels were measured by ELISA on Day 15 (not shown) and Day 29. Eight animals were studied per group for each treatment and condition. Data were analyzed using GraphPad Prism software and nonparametric analysis (Kruskal Wallis with Dunns multiple comparison post hoc tests). This study showed that ACTHAR® (adrenocorticotropic hormone) attenuated antigen-specific antibody production in vivo (FIG. 4).

Example 9: Matrix Protein Content

This study was performed to evaluate the effects of porcine $ACTH_{1-39}$ ($pACTH_{1-39}$ supplied by Bachem. DE), in an in vitro cell model of fibrosis. $pACTH_{1-39}$ was tested for its ability to inhibit TGFβ1-induced differentiation of normal human lung fibroblasts (NHLF) into fibrogenic myofibroblasts producing extracellular matrix (collagen). At day 1 the cells were seeded, at day 2 FBS medium was changed from 10% FBS to 0.1% FBS, at day 3 the medium was replaced with fresh medium and stimuli and different treatment concentrations were added to the cells, and at day 7 the cells were collected and analyzed for matrix protein content.

Figure 5:
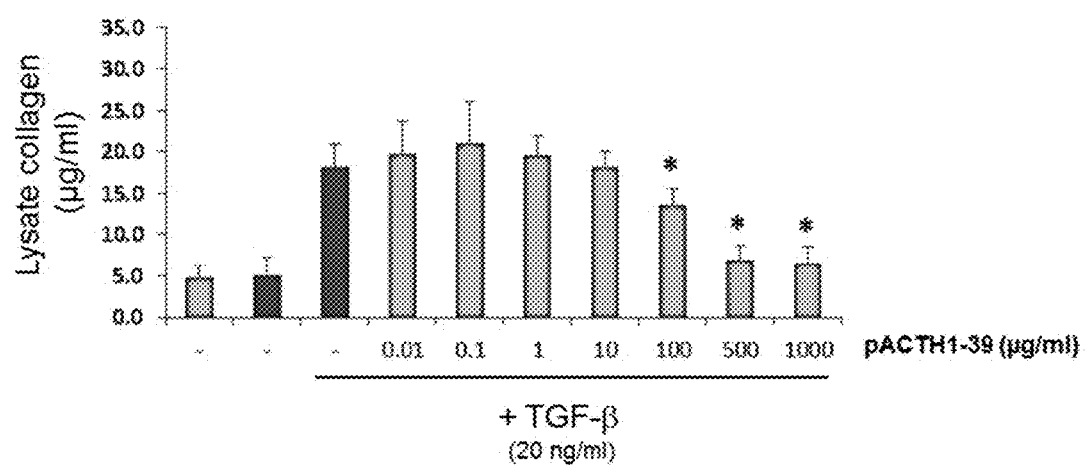
FIG. 5, described in Example 9, illustrates the effect of pACTH$_{1-39}$ in an in vitro cell model of fibrosis.

The matrix protein content in the culture medium was determined at day 4, and was measured using a Sirius Red based assay (soluble collagen assay kit from QuickZyme). The values were expressed in µg matrix protein per well (based on a collagen standard). Data were analyzed using GraphPad Prism software and nonparametric analysis (Kruskal Wallis with Dunns multiple comparison post hoc tests). The results demonstrated that $pACTH_{1-39}$ attenuated in vitro lung-specific fibrogenic potential (FIG. 5).

Example 10: LPS-Induced Acute Lung Injury In Vivo

Patients with ARDS typically have increased levels of inflammatory mediators such as IL-6 and IL-8 in lung lining fluid as well as in the circulation. High titer of autoantibodies to a number of cytokines have also been detected. These antibodies may be biomarkers for the high levels of cytokines which may cause autoimmunization and possibly contribute to immune dysfunction observed in ARDS (Journal of Translational Medicine, 2010, 8, 97). ARDS is associated with high capillary alveolar permeability to proteins (Crit. Care Med., 2001, 29, 10). Different strategies have been developed in order to reproduce the features of human ARDS in animals. One such strategy for modeling the disease is to injure the lung directly by a noxious stimulus, including the intratracheal or intranasal administration of bacteria or bacterial products such as LPS, since intra- or extra-pulmonary sepsis is the most common risk factor for the development of ARDS.

Figure 7:
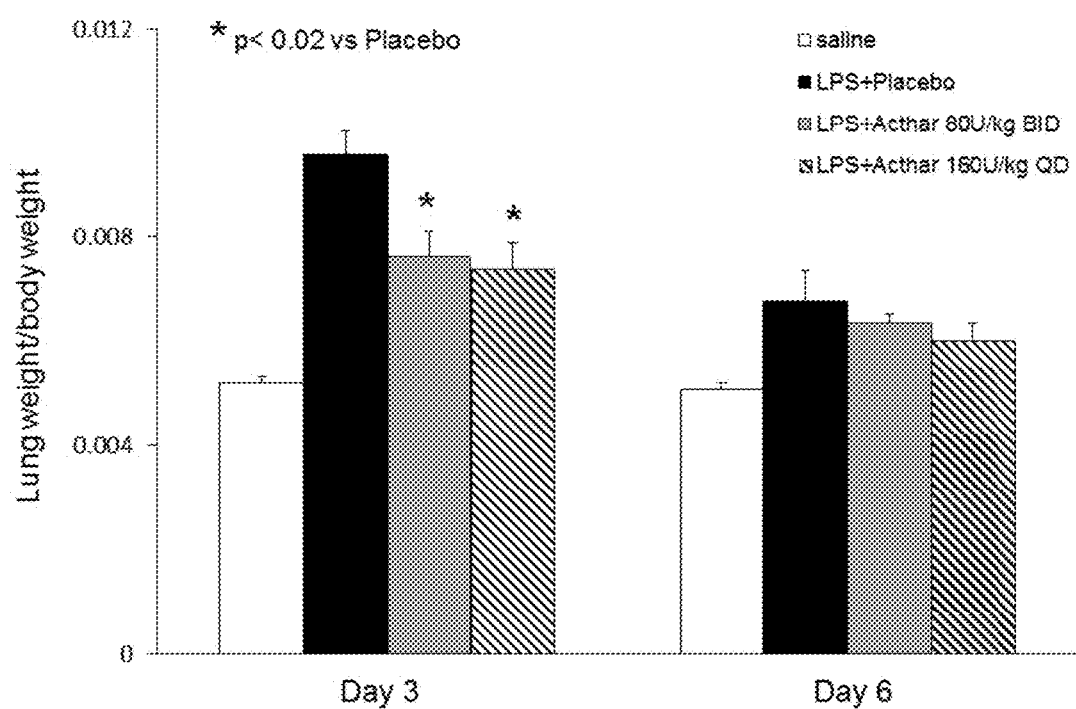
FIG. 7, described in Example 10, illustrates the effect of ACTHAR® (adrenocorticotropic hormone) on edema formation after LPS-induced acute lung injury.
Figure 8:
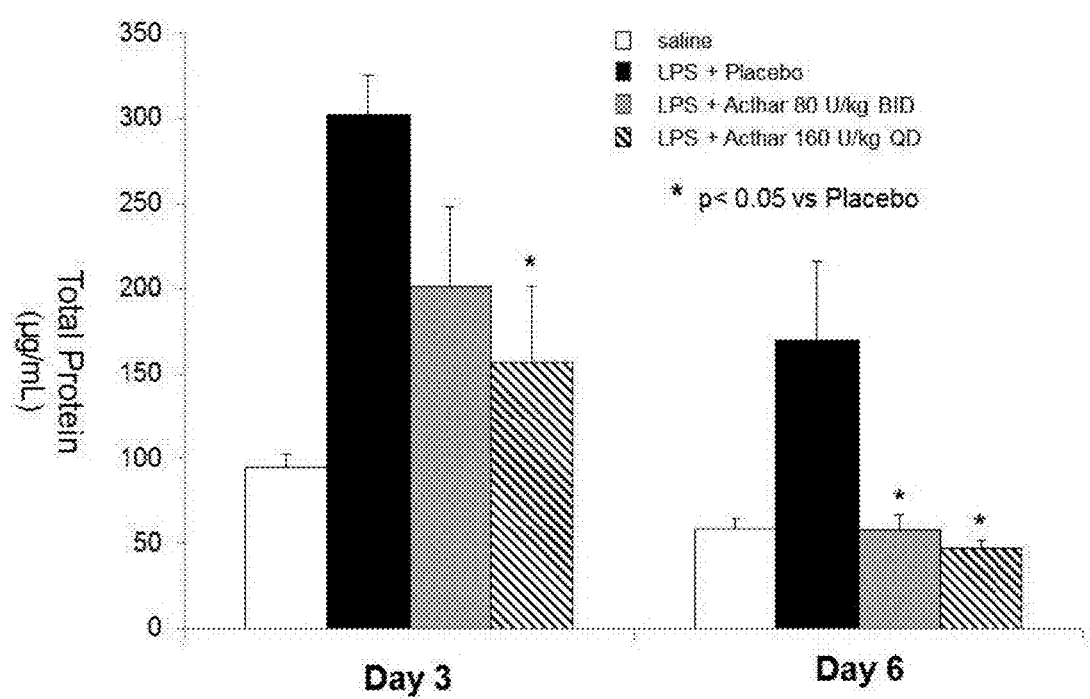
FIG. 8, described in Example 10, illustrates the effect of ACTHAR® (adrenocorticotropic hormone) on alveolo-capillary permeability following LPS-induced acute lung injury.
Figure 9:
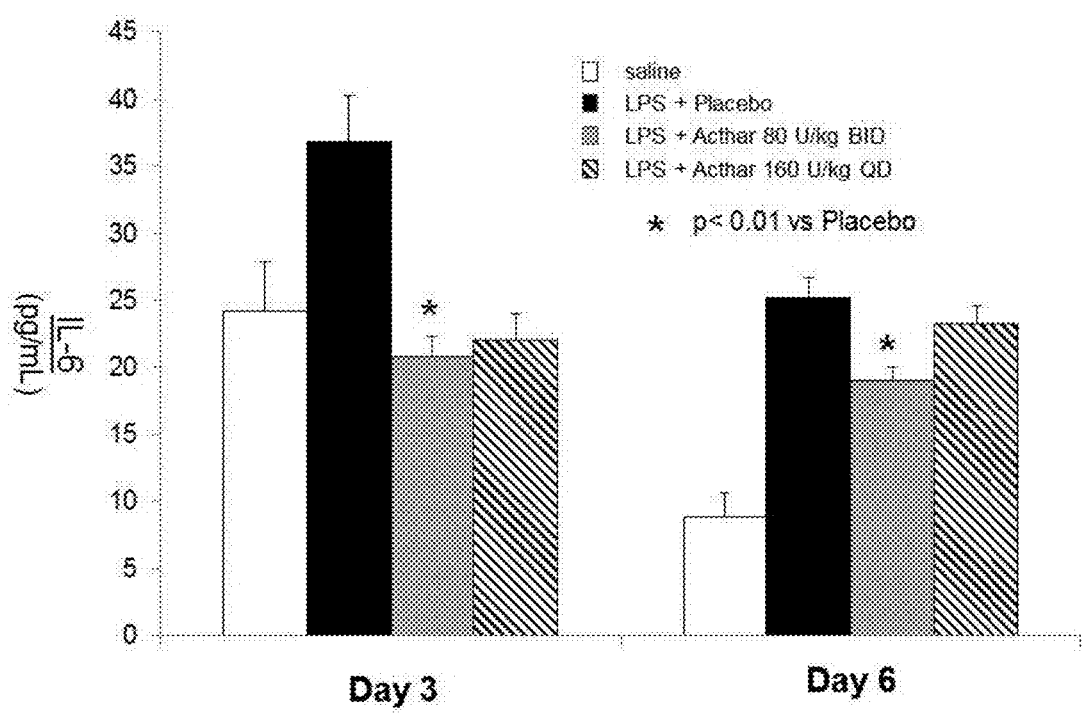
FIG. 9, described in Example 10, illustrates the effect of ACTHAR® (adrenocorticotropic hormone) on airspace inflammation after LPS-induced acute lung injury.

An in vivo model was used to evaluate ACTHAR® (adrenocorticotropic hormone) gel as a potential treatment for human ARDS. A single IT instillation of LPS (4 mg/kg) was administered to Sprague Dawley rats (~250 g, 8-9 weeks of age) to induce lung injury. Following LPS-instillation, placebo gel or ACTHAR® (adrenocorticotropic hormone) gel was administered subcutaneously either daily (placebo gel or 160 U/kg ACTHAR® (adrenocorticotropic hormone) gel) or twice daily (80 U/kg ACTHAR® (adrenocorticotropic hormone) gel) for up to 14 days. Separate groups of rats (n=6) were sacrificed on Days 1, 2, 3, 6, and 14 in order to evaluate the time course of LPS-induced lung injury, and to evaluate the effects of ACTHAR® (adrenocorticotropic hormone) on injury severity as a function of time. Outcome data included clinical observations and measurement of lung edema as assessed by total protein concentration in bronchial alveolar lavage (BAL) fluid and lung weight/body weight ratio 3 and 6 days after administration of IT LPS. In addition, effects of ACTHAR® (adrenocorticotropic hormone) treatment on attenuation of airspace inflammation were assessed by measurement of the concentration the pro-inflammatory cytokine IL-6 in BAL fluid. Data were analyzed using GraphPad Prism software and nonparametric analysis (Kruskal Wallis with Dunns multiple comparison post hoc tests). Early in the course of lung injury (Days 1 and 2 post IT LPS), no significant differences in these outcome measures were observed (data not shown). This series of experiments showed that ACTHAR® (adrenocorticotropic hormone) increased the number of animals with no abnormal clinical phenotype after LPS-induced acute lung injury (FIG. 6), that ACTHAR® (adrenocorticotropic hormone) attenuated edema formation after LPS-induced acute lung injury (FIG. 7), that ACTHAR® (adrenocorticotropic hormone) attenuated alveolo-capillary permeability following LPS-induced acute lung injury (FIG. 8), and that ACTHAR® (adrenocorticotropic hormone) attenuated airspace inflammation after LPS-induced acute lung injury (FIG. 9).

REFERENCES

Hofmann, et al. P.N.A.S., Vol. 67, No. 2, pp. 829-836, October 1970.
Johnson, et al., Acute Lung Injury: Epidemiology, Pathogenesis, and Treatment J Aerosol Med Pulm Drug Deliv. August 2010; 23(4): 243-252
Ware L B, Matthay M A. The acute respiratory distress syndrome. N Engl J Med 2000; 342:1334-49
Cushing's Syndrome (Monographs on Endocrinology) Volume 22, 1982, pp 23-32
CH. 3. ACTH Action Dorothy T. Krieger M. D.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating an individual diagnosed with or suspected of having acute respiratory distress syndrome (ARDS) comprising administration of a therapeutically effective amount of an adrenocorticotropic hormone (ACTH) peptide to an individual in need thereof, wherein the ACTH peptide is an $ACTH_{1-39}$ peptide having the sequence:

```
                                              (SEQ ID NO: 1)
H-Ser-Tyr-Ser-Met-Glu-His-Phe-Arg-Trp-Gly-
   1   2   3   4   5   6   7   8   9  10

Lys-Pro-Val-Gly-Lys-Lys-Arg-Arg-Pro-Val-
 11  12  13  14  15  16  17  18  19  20

Lys-Val-Tyr-Pro-X_{aa1}-Gly-Ala-Glu-Asp-X_{aa2}-
 21  22  23  24    25   26  27  28  29   30

Leu-Ala-Glu-Ala-Phe-Pro-Leu-Glu-Phe-OH
 31  32  33  34  35  36  37  38  39
``` wherein $X_{aa1}$ is Asp or Asn; and $X_{aa2}$ is Gln or Glu.

2. The method of claim 1, wherein the ACTH peptide is administered in an initial phase of from one to five doses at daily intervals and a subsequent phase of one or more doses administered at intervals greater than one day.

3. The method of claim 2, wherein each of the one to five doses of the initial phase is between about 10 U and about 100 U.

4. The method of claim 2, wherein each of the one or more doses of the subsequent phase is between about 30 U and about 100 U.

5. The method of claim 2, wherein each of the one to five doses of the initial phase is between about 30 U and about 100 U, and each of the one or more doses of the subsequent phase is between about 20% and about 100% of each of the one to five doses of the initial phase.

6. The method of claim 2, wherein each of the one to five doses of the initial phase is between about 45 U and about 100 U, and each of the one or more doses of the subsequent phase is between about 10 U and about 80 U.

7. The method of claim 2, wherein each of the one to five doses of the initial phase is between about 60 U and about 100 U, and each of the one or more doses of the subsequent phase is between about 20 U and about 60 U.

8. The method of claim 2 wherein each of the one to five doses of the initial phase is about 64 U, and each of the one or more doses of the subsequent phase is about 32 U.

9. The method of claim 8, wherein the one or more doses of the subsequent phase are administered at intervals selected from the group consisting of every two days, every three days, every four days, every 5 days, every 6 days, once a week, and every two weeks.

10. The method of claim 1, wherein the ACTH peptide is formulated as an injectable solution, immediate release formulation, prolonged release formulation, controlled release formulation, delayed release formulation, pulsatile release formulation, multiparticulate formulation or mixed immediate and controlled release formulation.

11. The method of claim 1, wherein the ACTH peptide is formulated as a gel.

12. The method of claim 10, wherein the ACTH peptide is administered intramuscularly, subcutaneously, intravenously, systemically, transmucosally, parenterally, intranasally, buccally, transdermally, rectally, by inhalation or by implant.

13. The method of claim 11, wherein the ACTH peptide is administered by injection intramuscularly.

14. The method claim 1, wherein the ACTH peptide is administered intravenously.

15. The method of claim 1, wherein the ACTH peptide is a recombinant ACTH peptide.

16. The method of claim 1, wherein the ACTH peptide is a porcine-derived ACTH peptide.

17. The method of claim 1, wherein the ACTH peptide is a synthetic ACTH peptide.

18. The method of claim 1, further comprising administration of a second therapeutic treatment, wherein the second therapeutic treatment is administered sequentially or simultaneously.

19. The method of claim 18, wherein the second therapeutic treatment is ventilation, a glucocorticoid, a surfactant, inhaled nitric oxide, an antioxidant, a protease inhibitor, a recombinant human activated protein C, a β2-agonist, lisofylline, a statin, inhaled heparin, a diuretic, a sedative, an analgesic, a muscle relaxant, an antibiotic, inhaled prostacyclin, inhaled synthetic prostacyclin analog, ketoconazole, alprostadil, keratinocyte growth factor, a beta-agonist, human monoclonal antibody (mAb) against tissue factor VIIa (TS factor 7a), an interferon receptor agonist, insulin, perfluorocarbon, budesonide, recombinant human angiotensin-converting enzyme (ACE), recombinant human Clara cell 10 kDa (CC10) protein, tissue plasminogen activator, human mesenchymal stem cells, or nutritional therapy.

20. The method of claim 18, wherein the second therapeutic treatment is methylprednisolone, dexamethasone, prednisone, prednisolone, betamethasone, triamcinolone, triamcinolone acetonide, beclometasone, albuterol, lisofylline, rosuvastatin, inhaled heparin, inhaled nitric oxide, recombinant human activated protein C, ibuprofen, naproxen, acetaminophen, cisatracurium besylate, procysteine, acetylcysteine, inhaled prostacyclin, ketoconazole, alprostadil, keratinocyte growth factor, a beta-agonist, human monoclonal antibody (mAb) against tissue factor VIIa (TS factor 7a), insulin, perfluorocarbon, budesonide, recombinant human angiotensin-converting enzyme (ACE), recombinant human Clara cell 10 kDa (CC10) protein, tissue plasminogen activator, human mesenchymal stem cells, nutritional therapy, a combination of omega-3 fatty acids, an antioxidant, γ-linolenic acids with isocaloric foods, or mechanical ventilation.

21. The method of claim 1, wherein the ACTH peptide is SEQ ID NO: 2, SEQ ID NO: 3, SEQ ID NO: 4, or SEQ ID NO: 5.

* * * * *

SEQUENCE LISTING

```
<160> NUMBER OF SEQ ID NOS: 9

<210> SEQ ID NO 1
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (25)..(25)
<223> OTHER INFORMATION: Xaa is Asp or Asn
<220> FEATURE:
<221> NAME/KEY: MISC_FEATURE
<222> LOCATION: (30)..(30)
<223> OTHER INFORMATION: Xaa is Gln or Glu
```

```
<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Xaa Gly Ala Glu Asp Xaa Leu Ala
            20                  25                  30

Glu Ala Phe Pro Leu Glu Phe
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Gln Leu Ala
            20                  25                  30

Glu Ala Phe Pro Leu Glu Phe
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic peptide

<400> SEQUENCE: 3

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Leu Ala
            20                  25                  30

Glu Ala Phe Pro Leu Glu Phe
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic peptide

<400> SEQUENCE: 4

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Glu Leu Ala
            20                  25                  30

Glu Ala Phe Pro Leu Glu Phe
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic peptide
```

```
<400> SEQUENCE: 5

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Gln Leu Ala
            20                  25                  30

Glu Ala Phe Pro Leu Glu Phe
        35

<210> SEQ ID NO 6
<211> LENGTH: 24
<212> TYPE: PRT
<213> ORGANISM: Artificial Sequence
<220> FEATURE:
<223> OTHER INFORMATION: Synthetic peptide

<400> SEQUENCE: 6

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Ser Tyr Ser Met Glu His Phe Arg Trp Gly Lys Pro Val Gly Lys Lys
1               5                   10                  15

Arg

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (13)..(13)
<223> OTHER INFORMATION: C-terminal NH2

<400> SEQUENCE: 8

Ser Tyr Ser Met Glu His Phe Arg Trp Gly Lys Pro Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Ser Tyr Ser Met Glu His Phe Arg Trp Gly Lys Pro Val
1               5                   10
```